United States Patent
Yamazaki

(10) Patent No.: US 9,271,919 B2
(45) Date of Patent: Mar. 1, 2016

(54) HAIR TREATMENT AGENT COMPOSITION

(75) Inventor: Naoyuki Yamazaki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 116 days.

(21) Appl. No.: 13/976,782

(22) PCT Filed: Dec. 27, 2011

(86) PCT No.: PCT/JP2011/080347
§ 371 (c)(1),
(2), (4) Date: Jun. 27, 2013

(87) PCT Pub. No.: WO2012/091074
PCT Pub. Date: Jul. 5, 2012

(65) Prior Publication Data
US 2013/0295030 A1   Nov. 7, 2013

(30) Foreign Application Priority Data

Dec. 28, 2010  (JP) .................... 2010-294132
May 2, 2011    (JP) .................... 2011-103315

(51) Int. Cl.
*A61K 8/73* (2006.01)
*A61Q 5/00* (2006.01)
*A61Q 5/02* (2006.01)
*A61Q 5/10* (2006.01)
*A61Q 5/04* (2006.01)
*A61Q 5/12* (2006.01)
*C08B 11/193* (2006.01)
*C08L 1/26* (2006.01)
*C08L 1/28* (2006.01)

(52) U.S. Cl.
CPC . *A61K 8/731* (2013.01); *A61Q 5/00* (2013.01); *A61Q 5/02* (2013.01); *A61Q 5/04* (2013.01); *A61Q 5/10* (2013.01); *A61Q 5/12* (2013.01); *C08B 11/193* (2013.01); *C08L 1/26* (2013.01); *C08L 1/284* (2013.01)

(58) Field of Classification Search
None
See application file for complete search history.

(56) References Cited

U.S. PATENT DOCUMENTS

| | | | |
|---|---|---|---|
| 3,472,840 A | 10/1969 | Stone et al. | |
| 4,243,659 A * | 1/1981 | Balingit | A61K 8/23 424/70.2 |
| 4,298,494 A | 11/1981 | Parslow et al. | |
| 4,364,837 A | 12/1982 | Pader | |
| 5,254,333 A * | 10/1993 | Kajino et al. | 424/70.11 |
| 6,217,855 B1 * | 4/2001 | Itou et al. | 424/70.2 |
| 6,251,145 B1 | 6/2001 | De La Mettrie et al. | |
| 2003/0091521 A1 * | 5/2003 | Midha | A61K 8/25 424/70.1 |
| 2010/0247346 A1 | 9/2010 | Hasegawa | |
| 2010/0274001 A1 | 10/2010 | Okutsu et al. | |
| 2012/0230934 A1 * | 9/2012 | Doi et al. | 424/70.13 |

FOREIGN PATENT DOCUMENTS

| | | |
|---|---|---|
| EP | 0093601 A2 | 11/1983 |
| EP | 0149249 A2 | 7/1985 |
| JP | 45-20318 B1 | 7/1970 |
| JP | 53-90368 A | 8/1978 |
| JP | 56-92810 A | 7/1981 |
| JP | 58-53996 A | 3/1983 |
| JP | 58-35640 B2 | 8/1983 |
| JP | 59-42681 B2 | 10/1984 |
| JP | 60-170601 A | 9/1985 |
| JP | 60-46158 B2 | 10/1985 |
| JP | 62-236801 A | 10/1987 |
| JP | 4-108723 A | 4/1992 |
| JP | 6-48916 A | 2/1994 |
| JP | 2003-64184 A | 3/2003 |
| JP | 3472491 B2 | 12/2003 |
| JP | 2004-331918 A | 11/2004 |
| JP | 2007-120415 A | 5/2007 |
| JP | 2009-143997 A | 7/2009 |
| WO | WO 2011/059063 * | 5/2011 ............... A61K 8/73 |

OTHER PUBLICATIONS

International Search Report for Application No. PCT/JP2011/080347 dated Apr. 17, 2012.
A Chinese Office Action, dated Mar. 9, 2015, for Chinese Application No. 201180063680.6 is provided.
An English translation of JP-53-90368-A, published on Aug. 9, 1978.
An Office Action issued in the corresponding Korean Patent Application No. 10-2013-7016767 on Jun. 6, 2015.

* cited by examiner

*Primary Examiner* — Brian Gulledge
(74) *Attorney, Agent, or Firm* — Birch, Stewart, Kolasch & Birch, LLP

(57) ABSTRACT

The present invention relates to a hair treatment composition capable of imparting good finger combability, body and manageability to the hair treated therewith and dried, and to a method for producing the composition. The hair treatment composition contains a cationized hydroxypropyl cellulose (A) and at least one treating agent (B) selected from a hair-coloring dye, an oxidizing agent, an alkali agent and a keratin-reducing agent.

13 Claims, No Drawings

HAIR TREATMENT AGENT COMPOSITION

FIELD OF THE INVENTION

The present invention relates to a hair treatment composition and to a method for producing the composition.

BACKGROUND OF THE INVENTION

Recently, with the growing diversity of various hair styles, hair has become often damaged by chemical treatment with hair color, hair bleach, permanent wave agent, straight perm agent, sustainable hair set agent, hair relaxer, etc., or by daily hair care action of over-brushing or blowing, or by living environments exposed to UV rays, etc. Consequently, various ideas have been devised for hair treatment compositions to coat the surface of hair to thereby restore a silky feeling of hair.

For example, for improving finger combability, softness, manageability and the like of hair, a hair conditioner contains a cationized polymer, and an oil such as a silicone, an ester oil, a mineral oil or the like. However, when the amount of the additives is increased, then the hair treated with the conditioner would get an oily sensation after dried, and the feeling in use of the conditioner may worsen; but when the amount is decreased, then the conditioning effect would be insufficient.

Consequently, a hair treatment composition having a high conditioning effect is desired.

For example, Patent Reference 1 discloses a hair color/bleach composition excellent in miscibility of the base material and improved in the feeling in rinsing and in the hair touch after treating, which includes a first pack containing a cellulosic polymer such as hydroxypropyl cellulose or the like, an alkali agent, a cationic surfactant and a higher alcohol and having a pH of from 8 to 13, and a second pack containing an oxidizing agent and having a pH of from 2 to 5.

Patent Reference 2 discloses a method for producing a cation-modified cellulose derivative such as a cationized hydroxypropyl cellulose or the like, saying that the derivative can be used as an additive to cosmetics, shampoo, rinse, treatment, etc.

Patent Reference 3 discloses a hair spray composition containing a cationized hydroxypropyl cellulose and an alcohol solvent.

CITATION LIST

Patent References

Patent Reference 1: JP-A 2007-126415
Patent Reference 2: JP-A 53-90368
Patent Reference 3: JP-A 60-170601

SUMMARY OF THE INVENTION

The present invention relates to the following (1) and (2):
(1) A hair treatment composition containing a cationized hydroxypropyl cellulose (A) and at least one treating agent (B) selected from a hair-coloring dye, an oxidizing agent, an alkali agent and a keratin-reducing agent.
(2) A method for producing a hair treatment composition containing a cationized hydroxypropyl cellulose (A) and at least one treating agent (B) selected from a hair-coloring dye, an oxidizing agent, an alkali agent and a keratin-reducing agent; the method including specific steps.

DETAILED DESCRIPTION OF THE INVENTION

Conventional hair treatment agents are not sufficiently satisfactory in point of the feeling in use thereof such as the hair finger combability and manageability after drying, and it is desired to develop a hair treatment composition having a further higher conditioning effect.

The present invention relates to a hair treatment composition capable of imparting good finger combability, body and manageability to the hair treated therewith and dried, and to a method for producing the composition.

The present inventors have found that the above-mentioned problems can be solved by incorporating a specific cationized hydroxypropyl cellulose to a hair cosmetic.

Specifically, the present invention relates to the following (1) and (2):
(1) A hair treatment composition containing a cationized hydroxypropyl cellulose (A) and at least one treating agent (B) selected from a hair-coloring dye, an oxidizing agent, an alkali agent and a keratin-reducing agent.
(2) A method for producing a hair treatment composition containing a cationized hydroxypropyl cellulose (A) and at least one treating agent (B) selected from a hair-coloring dye, an oxidizing agent, an alkali agent and a keratin-reducing agent; the method including the following steps (a-1) to (a-3), the following steps (b-1) to (b-4), or the following steps (c-1) to (c-4):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A), Step (b-1): a step of processing a cellulose-containing raw material with a grinder to give a cellulose-containing raw material in which the cellulose has a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) and propylene oxide to give a hydroxypropyl cellulose, Step (b-4): a step of reacting the hydroxypropyl cellulose obtained in the step (b-3) with a cationizing agent to give the cationized hydroxypropyl cellulose (A), Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 µm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

According to the present invention, there can be provided a hair treatment composition capable of giving good finger combability, body and manageability to the hair treated therewith and dried, and a method for producing the composition.

[Hair Treatment Composition]

The hair treatment composition of the present invention contains a cationized hydroxypropyl cellulose (A) and at least one treating agent (B) selected from a hair-coloring, an oxidizing agent, an alkali agent and a keratin-reducing agent.

<Cationized Hydroxypropyl Cellulose (A)>

In the present invention, the cationized hydroxypropyl cellulose (A) (hereinafter this may be referred to as "C-HPC") means a cellulose having a cationic group and a propyleneoxy group. The cationic group is preferably a quaternary ammonium group.

Preferably, C-HPC has an anhydroglucose-derived main chain represented by the following general formula (1), in which the mean molar number of the cationized ethyleneoxy groups per the anhydroglucose unit is from 0.01 to 2.9 and the mean molar number of the propyleneoxy groups is from 0.1 to 4.0.

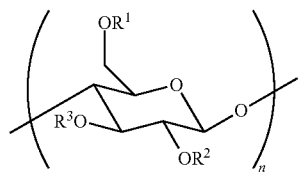
(1)

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 50 to 5000.)

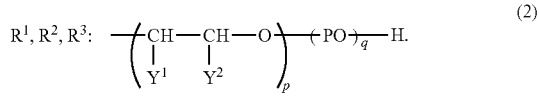
(2)

(In the formula, one of $Y^1$ and $Y^2$ is a hydrogen atom and the other is a cationic group represented by the following general formula (3); PO represents a propyleneoxy group; p indicates the number of cationized ethyleneoxy groups (—CH($Y^1$)—CH($Y^2$)—O—) in the general formula (2) and q indicates the number of propyleneoxy groups (—PO—) therein, each representing 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer.)

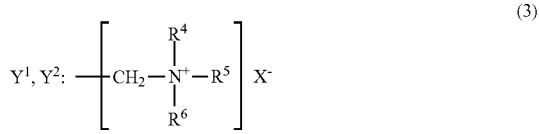
(3)

(In the formula, $R^4$, $R^5$ and $R^6$ each independently represent a linear or branched alkyl group having from 1 to 3 carbon atoms, and $X^-$ represents an anionic group.)

(Anhydroglucose-Derived Main Chain Represented by General Formula (1))

The anhydroglucose-derived main chain represented by the general formula (1) has, as shown in the following general formula (1), a main chain derived from an anhydroglucose.

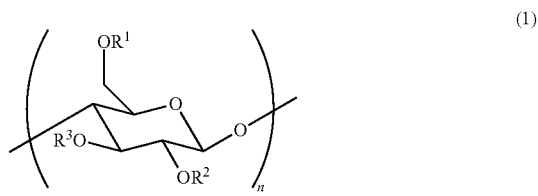
(1)

In the general formula (1), $R^1$, $R^2$ and $R^3$ each independently represent a substituent represented by the general formula (2), and $R^1$, $R^2$ and $R^3$ may be the same or different. n $R^1$'s, n $R^2$'s and n $R^3$'s each may be the same or different.

From the viewpoint of the capability of the hair treatment composition of the present invention to give good finger combability, body and manageability to the hair treated therewith and dried, the mean degree of polymerization n in the general formula (1) is preferably at least 50, more preferably at least 200, even more preferably at least 300, furthermore preferably at least 400. From the same viewpoint as above and from the viewpoint of reducing the viscosity of the hair treatment composition, the mean degree of polymerization n is preferably at most 5000, more preferably at most 2000, even more preferably at most 1500, further more preferably at most 1000.

Summing up these viewpoints, the mean degree of polymerization n is preferably from 50 to 5000, more preferably from 200 to 2000, even more preferably from 300 to 1500, further more preferably from 400 to 1000.

The mean degree of polymerization is a viscosity-average degree of polymerization to be determined according to a copper-ammonia process, and is concretely calculated according to the method described in the section of Examples.

(Substituent Represented by General Formula (2))

The substituent represented by the general formula (2) has, as shown in the following formula (2), a cationized ethyleneoxy group and a propyleneoxy group.

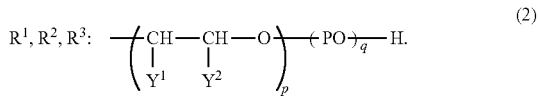
(2)

In the general formula (2), one of $Y^1$ and $Y^2$ is a hydrogen atom and the other is a cationic group represented by the following general formula (3), and PO represents a propyleneoxy group.

p indicates the number of cationized ethyleneoxy groups (—CH($Y^1$)—CH($Y^2$)—O—) in the general formula (2), and is 0 or a positive integer. From the viewpoint of easiness in production, p is preferably an integer of from 0 to 3, more preferably an integer of from 0 to 2, even more preferably 0 or 1.

q indicates the number of propyleneoxy groups (—PO—) in the general formula (2), and is 0 or a positive integer. From the viewpoint of easiness in production, q is preferably an integer of from 0 to 4, more preferably an integer of from 0 to 2, even more preferably 0 or 1.

In case where C-HPC has multiple substituents each represented by the general formula (2) in the molecule thereof, the values of p and q may differ between the substituents.

The total of p and q is preferably an integer of from 1 to 5 from the viewpoint of easiness in production, more preferably from 1 to 4, even more preferably from 1 to 3, further more preferably 1 or 2.

In case where both of p and q are not 0, the addition sequence of the cationized ethyleneoxy group and the propyleneoxy group is not defined, but from the viewpoint of easiness in production, the addition sequence is preferably as in the general formula (2).

In case where both p and q are not 0 and where p and/or q are/is 2 or more, the binding form may be any of like a block co-polymer or like a random co-polymer, but from the viewpoint of easiness in production, preferred is the binding form like a block co-polymer.

In at least one of n $R^1$'s, n $R^2$'s and n $R^3$'s, p in the general formula (2) is not 0, and in at least one of these, q in the general formula (2) is not 0.

(Cationic Group Represented by General Formula (3))

The cationic group represented by the general formula (3) has the structure of the formula (3) shown below.

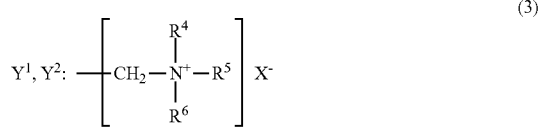

In the general formula (3), $R^4$, $R^5$ and $R^6$ each independently represent a linear or branched alkyl group having from 1 to 3 carbon atoms, and examples thereof include a methyl group, an ethyl group, an n-propyl group and an isopropyl group. Of those, preferred is a methyl group or an ethyl group from the viewpoint of the solubility of C-HPC in water, and more preferred is a methyl group.

In the general formula (3), $X^-$ represents an anionic group as a counter ion to the ammonium group. Not specifically defined, $X^-$ may be any anionic group. Specific examples of the group include an alkylsulfate ion, a sulfate ion, a phosphate ion, an alkylcarbonate ion, a halide ion, etc. Of those, preferred is a halide ion from the viewpoint of easiness in production. The halide ion includes a fluoride ion, a chloride ion, a bromide ion and an iodide ion. From the viewpoint of the solubility in water and the chemical stability of C-HPC, preferred is a chloride ion or a bromide ion, and more preferred is a chloride ion.

In C-HPC represented by the general formula (1), the degree of substitution with cationized ethyleneoxy group is preferably at least 0.01, more preferably at least 0.1, even more preferably at least 0.2, further more preferably at least 0.3 from the viewpoint that the hair treatment composition of the invention can give good finger combability, body and manageability to the hair treated therewith and dried; and the degree is still more preferably at least 0.8 from the viewpoint that the composition can give better finger combability to hair. Also from the viewpoint that the composition can give good finger combability to the hair treated therewith and dried and from the viewpoint of easiness in production, the degree is preferably at most 2.9, more preferably at most 2.5, even more preferably at most 2.0, further more preferably at most 1.5, still more preferably at most 1.2.

Summing up these viewpoints, the degree of substitution with cationized ethyleneoxy group is preferably from 0.01 to 2.9, more preferably from 0.1 to 2.5, even more preferably from 0.2 to 2.0, further more preferably from 0.3 to 1.5, still more preferably from 0.8 to 1.2.

In the present invention, the "degree of substitution with cationized ethyleneoxy group" means the mean molar number of the cationized ethyleneoxy groups existing in the molecule of C-HPC per mol of the anhydroglucose unit (hereinafter this may be referred to as "AGU") that constitutes the cellulose main chain. The degree of substitution with cationized ethyleneoxy group may be determined according to the method described in the section of Examples given below.

From the viewpoint of good finger combability, body and manageability of the hair treated with the hair treatment composition of the present invention and dried, the degree of substitution with propyleneoxy group is preferably at least 0.1, and from the viewpoint of good finger combability of hair, the degree is preferably at least 0.2, more preferably at least 0.3, even more preferably at least 0.6, further more preferably at least 1.0. From the viewpoint of good manageability of the hair treated and dried, and from the viewpoint of easiness in production, the degree is preferably at most 4.0, more preferably at most 3.0, even more preferably at most 2.8, further more preferably at most 2.5, still more preferably at most 2.0.

Summing up these viewpoints, the degree of substitution with propyleneoxy group is preferably from 0.1 to 4.0, more preferably from 0.2 to 3.0, even more preferably from 0.3 to 2.8, further more preferably from 0.6 to 2.5, still more preferably from 1.0 to 2.0.

In the present invention, the degree of substitution with propyleneoxy group means the mean molar number of the propyleneoxy groups existing in the molecule of C-HPC per mol of AGU that constitutes the cellulose main chain. The degree of substitution with propyleneoxy group may be determined according to the method described in the section of Examples given below.

From the viewpoint of good manageability of hair treated and dried and from the viewpoint of easiness in production, the sum of the degree of substitution with cationized ethyleneoxy group and the degree of substitution with propyleneoxy group is preferably at most 3.5, more preferably at most 3.2, even more preferably at most 3.0, further more preferably at most 2.5. Also from the viewpoint of good finger combability, manageability and body of hair treated and dried, the sum is preferably at least 0.3, more preferably at least 1.5, even more preferably at least 2.0, further more preferably at least 2.2.

Summing up these viewpoints, the sum of the degree of substitution with cationized ethyleneoxy group and the degree of substitution with propyleneoxy group is preferably from 0.3 to 3.5, more preferably from 1.5 to 3.2, even more preferably from 2.0 to 3.0, further more preferably from 2.2 to 2.5.

The viscosity of an aqueous 2 mass % solution of C-HPC at 30° C. (hereinafter this may be simply referred to as "2% viscosity") is preferably from 2 to 30000 mPa·s, more preferably from 3 to 25000 mPa·s, even more preferably from 4 to 20000 mPa·s, further more preferably from 5 to 15000 mPa·s, from the viewpoint of the easiness in incorporating the components in the hair treatment composition and from the viewpoint of the storage stability of the composition. The 2% viscosity is a value to be determined according to the method described in the section of Examples.

[Production of C-HPC]

C-HPC can be obtained, for example, according to the following production methods (1) to (3):

(1) A method where cellulose is mixed with a large amount of water and a large excess of an alkali metal hydroxide in slurry and reacted with a cationizing agent and propylene oxide.

(2) A method where dimethylacetamide containing lithium chloride is used as a solvent and cellulose is dissolved therein along with an amine or an alcoholate catalyst added thereto, and reacted with a cationizing agent and propylene oxide.

(3) A method where any excessive water or solvent as in the above (1) or (2) is not used but powdery, pellet-like or chip-like cellulose is reacted with a cationizing agent and propylene oxide in the presence of a base.

In the above-mentioned production methods (1) to (3), any of the reaction with a cationizing agent and the reaction with propylene oxide may be carried out first or the two may be carried out simultaneously.

Of these production methods, preferred is the production method (3) from the viewpoint of the easiness in production. Specific examples of the production method for C-HPC according to the method (3) include (3-1) a method of cationizing and hydroxypropylating a cellulose-containing raw material, (3-2) a method of processing a cellulose-containing raw material to give an alkali cellulose and then cationizing and hydroxypropylating the resulting alkali cellulose.

The production method (3) is described concretely hereinunder.

[(3-1) Method of Cationizing and Hydroxypropylating Cellulose-Containing Raw Material]
<Cellulose-Containing Raw Material>

As the cellulose-containing raw material for producing C-HPC, preferably used here is (i) a cellulose-containing raw material having a lowered degree of crystallinity, for example, a low-crystalline powdery cellulose, or (ii) a cellulose-containing raw material having a high degree of crystallinity, for example, pulp.

<(3-1-i) Production of C-HPC Using Cellulose-Containing Raw Material Having Lowered Crystallinity>
(Production of Cellulose-Containing Raw Material Having Lowered Crystallinity)

A cellulose-containing raw material having a lowered crystallinity, for example, a low-crystalline powdery cellulose can be prepared from a sheet-like or a roll-like pulp having a high cellulose purity that is obtained as a general-purpose raw material. The production method for low-crystalline powdery cellulose is not specifically defined. For example, there are mentioned the methods described in JP-A 62-236801, 2003-64184, 2004-331918, etc. Of those, more preferred is using a low-crystalline or amorphous powdery cellulose obtained through mechanochemical treatment (hereinafter this may be generically referred to as "low-crystalline powdery cellulose") from the viewpoint of improving the productivity of the cellulose-containing raw material having a lowered crystallinity, for example, the low-crystalline powdery cellulose.

Here the "low crystallinity" of the low-crystalline powdery cellulose means that the cellulose has a large amorphous proportion in the crystal structure thereof. Concretely, from the viewpoint of increasing the reactivity of the material with a cationizing agent and propylene oxide, the degree of crystallinity thereof to be calculated by the math formula (1) mentioned below is preferably at most 30%, more preferably at most 20%, even more preferably at most 10%, and still more preferred is use of a completely amorphous cellulose of which the degree of crystallinity is nearly 0%.

Degree of Crystallinity (%)=$[(I_{22.6}-I_{18.5})/I_{22.6}]\times 100$     (1)

(In the formula, $I_{22.6}$ means the diffraction intensity at the lattice plane (002 plane) of a cellulose I-type crystal in X-ray diffractiometry (diffraction angle $2\theta=22.6°$), and $I_{18.5}$ means the diffraction intensity at the amorphous moiety (diffraction angle $2\theta=18.5°$).)

As the production method for low-crystalline powdery cellulose through mechanochemical treatment, for example, there is mentioned a method of processing a chip-like pulp obtained by roughly grinding a sheet-like pulp, using a grinder. Before the treatment with a grinder, the chip-like pulp may be processed through an extruder.

The extruder to be used in the method may be a single-screw or double-screw extruder, but preferred is a double-screw extruder. From the viewpoint of imparting strong compression shear force, preferred is an extruder equipped with a so-called kneading disc part in any part of the screw.

The processing method with an extruder is not specifically defined. Preferred is a method where a chip-like pulp is put into an extruder and continuously processed therein.

The grinder includes a roll mill such as a high-pressure compression roll mill, a roll-rotating mill, etc.; a vertical roller mill such as a ring roller mill, a roller-less mill, a boll-less mill, etc.; a chamber vibration-mediated mill such as a rotary ball mill, a vibratory ball mill, a vibratory rod mill, a vibratory tube mill, a planetary ball mill, a centrifugal fluidization mill, etc.; a medium stirring mill such as a column grinder, a stirring column mill, a ventilation column mill, an annular mill, etc.; a consolidation shear mill such as a high-speed centrifugal roller mill, an angmill, etc.; a mortar, a stone mill, etc. Of those, preferred is a chamber vibration-mediated mill or a medium stirring mill from the viewpoint of efficiently lowering the degree of crystallinity of cellulose and from the viewpoint of productivity, and more preferred is a chamber vibration-mediated mill. Even more preferred is a vibration mill such as a vibratory ball mill, a vibratory rod mill, a vibratory tube mill or the like, and still more preferred is a vibratory ball mill or a vibratory rod mill.

The treatment method may be any of a batch process or a continuous process.

The preferred range of the filling rate with media such as balls, rods or the like may vary depending on the type of the grinder, but is preferably within a range of from 10 to 97%, more preferably from 15 to 95%. When the filling rate falls within the range, then the contact frequency between the raw material pulp and the media may increase and the grinding efficiency can be thereby increased without interfering with the movement of media. Here the filling rate means the apparent volume of the media relative to the volume of the stirring area of the grinder.

In the case of a ball mill, the material of the balls to be used as the media is not specifically defined. For example, there may be mentioned iron, stainless, alumina, zirconia, etc. The outer diameter of the ball is preferably from 0.1 to 100 mm, more preferably from 1 to 50 mm from the viewpoint of efficiently lowering the degree of crystallinity of cellulose.

Also from the viewpoint of efficiently lowering the degree of crystallinity of cellulose, the treatment time in a grinder is preferably from 5 minutes to 72 hours, more preferably from 10 minutes to 30 hours. In treatment in a grinder, the temperature is preferably not higher than 250° C., more preferably from 5 to 200° C. from the viewpoint of minimizing the denaturation and degradation owing to heat generation.

Rods for use as the medium in the grinder are rod-shaped media, of which the cross section may be any of polygon such as tetragon, hexagon or the like, as well as circle, oval, etc.

The outer diameter of the rod is preferably from 0.5 to 200 mm, more preferably from 1 to 100 mm, even more preferably from 5 to 50 mm. The length of the rod is not specifically defined so far as it is shorter than the length of the chamber of the grinder. When the rod size falls within the above range, then a desired grinding force can be applied to cellulose by which the degree of crystallinity of the ground cellulose can be efficiently lowered.

Not specifically defined, the treatment time and the treatment temperature in the rods-filled vibration mill may be the same as the treatment time and the treatment temperature in the above-mentioned ball mill.

According to the above-mentioned methods, it is possible to control the molecular weight of cellulose, and a low-crystalline powdery cellulose having a high degree of polymerization and hardly available in general can be readily prepared. The mean degree of polymerization of the low-crystalline powdery cellulose for use herein is preferably from 100 to 2000, more preferably from 300 to 1500, even more preferably from 350 to 1350.

The mean particle size of the low-crystalline powdery cellulose is not specifically defined so far as the cellulose can maintain a good flowable state as powder. Preferably, the mean particle size is at most 300 μm, more preferably at most 150 μm, even more preferably at most 50 μm. From the viewpoint of improving the handleability of the powdery cellulose, the mean particle size thereof is preferably at least 20 μm, more preferably at least 25 μm. For evading mixing with a minor amount of coarse particles owing to aggregation, preferably used in the reaction are undersize particles having passed through a sieve having a sieve opening of from 300 to 1000 μm or so.

(Cationization of Cellulose-Containing Raw Material Having Lowered Crystallinity)

Produced in the manner as above, the cellulose-containing raw material having a lowered degree of crystallinity, for example, the low-crystalline powdery cellulose is reacted with a glycidyltrialkylammonium salt in the presence of a base for cationization to give a cationized cellulose.

The glycidyltrialkylammonium salt to be used as the cationizing agent includes glycidyltrimethylammonium chloride, glycidyltriethylammonium chloride, glycidyltrimethylammonium bromide, glycidyltriethylammonium bromide, etc. From the viewpoint of availability, preferred is glycidyltrimethylammonium chloride.

The amount of the glycidyltrialkylammonium salt to be added is preferably from 0.01 to 8.5 molar times per mol of AGU in cellulose, more preferably from 0.1 to 7 molar times, even more preferably from 0.2 to 5.5 molar times, still more preferably from 0.5 to 4.5 molar times, from the viewpoint of good finger combability, body and manageability of hair treated with the hair treatment composition and dried and from the viewpoint of easiness in production.

The base to be present in the system during cationization includes lithium hydroxide, sodium hydroxide, potassium hydroxide, calcium hydroxide, barium hydroxide, etc. From the viewpoint of availability, general versatility and economic potential, more preferred are sodium hydroxide and barium hydroxide.

The amount of the base to be added may vary depending on the type of cellulose, but from the viewpoint of efficiently reacting cellulose and the cationizing agent, the amount is, in general, preferably from 0.05 to 1.0 molar times relative to mol of AGU in cellulose, more preferably from 0.06 to 1.0 molar times, even more preferably from 0.07 to 0.7 molar times, still more preferably from 0.1 to 0.3 molar times.

The water content in the reaction system is preferably at most 100% by mass relative to the cellulose used as the raw material. When the water content relative to the cellulose falls within the range, then the cellulose would not aggregate excessively and therefore can be reacted as a flowable powdery state. From this viewpoint, the water content is preferably at most 80% by mass, more preferably from 5 to 50% by mass.

The reaction temperature is generally from 10 to 85° C., but preferably from 15 to 80° C.

(Hydroxypropylation of Cationized Cellulose)

Produced in the manner as above, the cationized cellulose is reacted with propylene oxide for hydroxypropylation to give C-HPC.

Here the amount of propylene oxide to be used is preferably from 0.01 to 8.5 molar times per mol of AGU in the cellulose molecule, more preferably from 0.1 to 5.0 molar times, even more preferably from 1.0 to 3.0 molar times, from the viewpoint of good finger combability, body and manageability of the hair treated with the hair treatment agent and dried.

As the catalyst for the hydroxypropylation, usable is a base or an acid. The base catalyst includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, triethylenediamine, etc. The acid catalyst includes Lewis acid catalysts such as lanthanide triflates, etc.

Of those, preferred is a base catalyst from the viewpoint of preventing the degree of polymerization of cellulose in the cellulose-containing staring material from lowering, and more preferred is an alkali metal hydroxide. Even more preferred is sodium hydroxide or potassium hydroxide. One or more different types of these catalysts may be used here either singly or as combined.

Not specifically defined, the amount of the catalyst to be used is, in general, preferably from 0.05 to 1.0 molar times per mol of AGU in the cellulose molecule, more preferably from 0.07 to 0.7 molar times, even more preferably from 0.1 to 0.3 molar times.

In case where the cationization step is carried out first, the base used in the cationization step may be used as such as the catalyst in the hydroxypropylation, and addition of any additional catalyst may be omitted in the hydroxypropylation step.

The method of adding propylene oxide is not specifically defined. For example, there are mentioned (a) a method of adding a catalyst to the cationized cellulose and then dropwise adding propylene oxide thereto, and (b) a method adding propylene oxide to the cationized cellulose all at a time and thereafter gradually adding thereto a catalyst to lead the reaction. More preferred is the method (a).

The water content in the reaction system is preferably at most 100% by mass relative to the cellulose used as the raw material. When the water content relative to the cellulose falls within the range, then the cationized cellulose would not aggregate excessively and therefore can be reacted as a flowable powdery state. From this viewpoint, the water content is preferably at most 80% by mass, more preferably from 5 to 50% by mass.

In the present invention, preferably, the cationized cellulose, the catalyst and the propylene oxide are reacted in a flowable powdery state. If desired, the cationized cellulose powder and the catalyst may be previously uniformly mixed and dispersed in a mixing apparatus such as a mixer or the like or by the use of a shaking machine, a mixing mill or the like, and thereafter propylene oxide may be added thereto and reacted.

Preferably, the reaction temperature in hydroxypropylation is from 0 to 150° C.; however, from the viewpoint of preventing polymerization of propylene oxide and preventing any rapid reaction, the temperature is more preferably from 10 to 100° C., even more preferably from 20 to 80° C. The reaction may be carried out under normal pressure.

From the viewpoint of evading the reduction in the molecular weight owing to cleavage of the cellulose chains during the reaction, it is desirable to carry out the reaction in an inert gas atmosphere such as nitrogen, etc.

After the reaction, the unreacted propylene oxide is removed, and thereafter if desired, the system is neutralized, then purified and dried to give C-HPC for use in the present invention.

The neutralization may be carried out under normal process. For example, in case where a base catalyst is used, a liquid acid such as acetic acid or the like, or a mixed solution of an acid and an inert organic solvent, or an aqueous acid solution may be added to the system for neutralization. The type of the acid is not specifically defined, and the acid may be suitably selected in consideration of corrosion of apparatus, etc. The purification may be carried out by the use of a solvent such as water-containing isopropanol, water-containing acetone solvent or the like and/or by washing with water, or through a dialytic membrane.

Regarding the sequence of the cationization and the hydroxypropylation in the above-mentioned <(3-1-i) Production of C-HPC using cellulose-containing raw material having lowered crystallinity>, the cellulose in the cellulose-containing raw material may be first hydroxypropylated and then cationized, or may be hydroxypropylated and cationized at one time.

From the viewpoint of controlling the degree of substitution with cationized ethyleneoxy group and propyleneoxy group, preferably, the cellulose in the cellulose-containing raw material is first cationized and then hydroxypropylated.

For the purpose of increasing the degree of substitution with cationized ethyleneoxy group, the cationized and hydroxypropylated system may be further again cationized.

In the cationization step and the hydroxypropylation step in the above-mentioned <(3-1-i) Production of C-HPC using cellulose-containing raw material having lowered crystallinity>, the cellulose skeleton to be the main chain is not substantially cleaved, and therefore the mean degree of polymerization of the C-HPC to be obtained could be approximated by the mean degree of polymerization of the powdery cellulose treated for lowering the crystallinity thereof.

<(3-1-ii) Production of C-HPC Using Cellulose-Containing Raw Material Having High Crystallinity>
(Cationization of Cellulose-Containing Raw Material Having High Crystallinity)

In case where a cellulose-containing raw material having a high crystallinity, for example, pulp (hereinafter the cellulose-containing raw material is typically pulp) is used as the cellulose-containing raw material, not using the above-mentioned cellulose-containing raw material having lowered crystallinity, for example, the low-crystalline powdery cellulose, preferably, the cellulose-containing raw material is processed for crystallinity reduction in cationization for the purpose of improving the reactivity of the material.

Concretely, a cationizing agent is added to the cellulose-containing raw material and treated in a grinder for crystallinity reduction, and thereafter a base is added thereto and treated in a grinder for crystallinity reduction while the cellulose-containing raw material is reacted with a cationizing agent thereby giving a cationized cellulose; or a base is added to the cellulose-containing raw material and treated in a grinder for crystallinity reduction, and thereafter a cationizing agent is added thereto and treated in a grinder for crystallinity reduction along with reaction of the cellulose-containing raw material and the cationizing agent thereby giving a cationized cellulose. From the viewpoint of obtaining C-HPC having a high degree of substitution with cationized ethyleneoxy group, preferably, a cationizing agent is added to the cellulose-containing raw material and treated in a grinder, and thereafter a base is added thereto and treated in a grinder, and further a cationizing agent is added thereto and treated in a grinder. Addition of the cationizing agent after addition of the base may be carried out in multiple stages.

From the viewpoint of the solubility in water of the C-HPC obtained through the cationization, preferably, a cationizing agent is first added to the cellulose-containing raw material and treated in a grinder for crystallinity reduction, and thereafter a base is added thereto and treated in a grinder for crystallinity reduction along with reaction of the cellulose-containing raw material and the cationizing agent.

The cellulose-containing raw material having a high crystallinity includes various types of wood chips; pulps such as wood pulp produced from wood, cotton linter pulp obtained from fibers around cotton seeds, etc.; papers such as newspaper, cardboard, magazine, high-quality paper, etc.; plant stems and leaves such as rice straws, corn stems, etc.; plant shells such as rice husks, palm shells, coconut husks, etc. From the viewpoint of high cellulose purity and productivity of C-HPC, preferred is wood pulp.

The shape of the pulp to be used as the cellulose-containing raw material is not specifically defined so far as not interfering with the introduction thereof into a production apparatus, but from the viewpoint of handleability thereof, preferred is use of sheet-like pulp, or pellet-like or chip-like pulp produced by cutting or roughly grinding sheet-like pulp, or powdery cellulose obtained by finely pulverizing pulp.

The degree of crystallinity of the pulp for use as the cellulose-containing raw material is not defined. However, in general, the treatment of cellulose for crystallinity reduction is accompanied by molecular weight reduction owing to cleavage of cellulose chains, and therefore the cellulose in the cellulose-containing raw material having a low crystallinity has a low molecular weight. Consequently, from the viewpoint of obtaining C-HPC having a high molecular weight, preferred is used of cellulose having a high crystallinity. On the contrary, cellulose having an extremely high crystallinity of more than 95%, as calculated according to the above-mentioned math formula (1), is hardly available. Accordingly, from the viewpoint of the degree of polymerization and the availability, the degree of crystallinity calculated according to the above-mentioned math formula (1) of the cellulose in the cellulose-containing raw material is preferably from 10 to 95%, more preferably from 30 to 90%, even more preferably from 60 to 80%.

The mean degree of polymerization of the cellulose in the cellulose-containing raw material is not defined; however, from the viewpoint of obtaining C-HPC having a high molecular weight, preferred is use of cellulose in a cellulose-containing raw material having a larger degree of polymerization. From this viewpoint, the mean degree of polymerization of the cellulose in the cellulose-containing raw material is preferably from 50 to 5000, more preferably from 100 to 2000.

Preferred embodiments of the type and the amount of the cationizing agent, the type of the base, the type of the grinder, and the method and the condition for crystallinity reduction are the same as those described in the section of the above-mentioned <(3-1-i) Production of C-HPC using cellulose-containing raw material having lowered crystallinity>, except the treatment time with grinder for crystallinity reduction and the amount of the base.

The treatment time with grinder for crystallinity reduction is preferably from 1 minute to 5 hours, more preferably from 2 minutes to 3 hours, even more preferably from 5 minutes to 2 hours, from the viewpoint of efficiently lowering the degree of crystallinity of the treated cellulose while preventing the degree of polymerization thereof from lowering.

The amount of the base is preferably from 0.05 to 1.5 molar times per mol of AGU in the cellulose in the cellulose-containing raw material, more preferably from 0.07 to 1.0 molar times, even more preferably from 0.1 to 0.6 molar times, from the viewpoint of efficiently reacting the cellulose with the cationizing agent.

The cationization may go on after addition of the cationizing agent and the base for crystallinity reduction, however, when the reaction is insufficient, it is desirable that the system is ripened at from 10 to 100° C., more preferably from 30 to 80° C. for promoting the reaction.

Even though the cationization is sufficient, a glycidyltrialkylammonium salt may be added to the system to ripen it, whereby a cationized cellulose having a high degree of cationized ethyleneoxy group can be obtained.

The amount of water in ripening and other preferred embodiments are the same as those for the above-mentioned cationization of low-crystalline powdery cellulose, except the point that a cellulose-containing raw material having a high degree of crystallinity is used in place of the low-crystalline powdery cellulose as the raw material.

From the viewpoint of evading the reduction in the molecular weight owing to cleavage of cellulose chains during reaction, the reaction is preferably carried out in an inert gas atmosphere such as nitrogen, etc.

(Hydroxypropylation of Cationized Cellulose)

The amount of propylene oxide to be used for hydroxypropylation of cationized cellulose in <(3-1-ii) Production of C-HPC using cellulose-containing raw material having high crystallinity: Method (a)>, as well as the catalyst, the reaction condition, the treatment after the reaction and other preferred embodiments are the same as those described for the hydroxypropylation in the above-mentioned <(3-1-i) Production of C-HPC using cellulose-containing raw material having lowered crystallinity>.

Regarding the sequence of cationization and hydroxypropylation in the above-mentioned <(3-1-ii) Production of C-HPC using cellulose-containing raw material having high crystallinity: Method (a)>, the hydroxypropylation of the cellulose-containing raw material may be carried out first and then the cationization may be carried out, or the two may be carried out simultaneously. From the viewpoint of controlling the degree of substitution with cationized ethyleneoxy group and propyleneoxy group, preferably, the cellulose-containing raw material is first cationized and then hydroxypropylated.

From the viewpoint of increasing the degree of substitution with cationized ethyleneoxy group, the cationized and hydroxypropylated system may be further again cationized.

[(3-2) Method of Processing Cellulose-Containing Raw Material to Give Alkali Cellulose and then Cationizing and Hydropropylating the Resulting Alkali Cellulose]

<Cellulose-Containing Raw Material>

As the cellulose-containing raw material for producing C-HPC, preferably used here is (i) a cellulose-containing raw material having a lowered degree of crystallinity or (ii) a cellulose-containing raw material having a high degree of crystallinity, like in [(3-1) Method of cationizing and hydroxypropylating cellulose-containing raw material].

<(3-2-i) Production of C-HPC Using Cellulose-Containing Raw Material Having Lowered Crystallinity: Method (b)>

(Production of Cellulose-Containing Raw Material Having Lowered Crystallinity)

The cellulose-containing raw material having a lowered crystallinity is the same as that described in <(3-1-i) Production of C-HPC using cellulose-containing raw material having lowered crystallinity>.

From the viewpoint of improving the productivity of the cellulose-containing raw material having a lowered crystallinity, preferred is one to be produced by grinding a high-crystalline cellulose-containing raw material, for example, wood pulp.

The degree of crystallinity of the cellulose-containing raw material having a lowered crystallinity is preferably from 10 to 50%, more preferably from 10 to 40%, even more preferably from 10 to 30%, from the viewpoint of increasing the reactivity between the alkali cellulose to be mentioned below and the cationizing agent and propylene oxide and from the viewpoint of increasing the degree of polymerization of the cellulose-containing raw material.

(Treatment of Cellulose-Containing Raw Material Having a Lowered Crystallinity to Give Alkali Cellulose)

The cellulose-containing raw material having a lowered crystallinity is mixed with a base and water to give an alkali cellulose.

The base includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, triethylenediamine, etc. Of those, preferred is an alkali metal hydroxide or an alkaline earth metal hydroxide. Even more preferred is an alkali metal hydroxide; and still more preferred is sodium hydroxide or potassium hydroxide. One or more different types of these bases may be used here either singly or as combined.

The amount of the base is preferably from 0.6 to 1.5 mols per mol of AGU that constitutes the cellulose in the cellulose-containing raw material, more preferably from 0.7 to 1.3 mols, even more preferably from 0.8 to 1.2 mols, from the viewpoint of increasing the yield of the alkali cellulose and from the viewpoint of improving the reactivity of the alkali cellulose and the cationizing agent and propylene oxide to be mentioned below.

The amount of water to be added is preferably from 20 to 100% by mass of the cellulose in the cellulose-containing raw material, more preferably from 25 to 70% by mass, even more preferably from 30 to 60% by mass, from the viewpoint of increasing the yield of the alkali cellulose and from the viewpoint of improving the reactivity of the alkali cellulose and the cationizing agent and propylene oxide to be mentioned below.

The method of mixing the cellulose-containing raw material having lowered crystallinity with a base and water is not specifically defined, but from the viewpoint of increasing the productivity, it is desirable to add a base and water to the cellulose-containing raw material having lowered crystallinity. Regarding the addition mode, all the components may be added at a time to the reactor, or divided portions thereof may be added thereto intermittently. As the case may be, a base and water may be previously mixed, and the resulting mixture may be sprayed onto the cellulose-containing raw material.

Not specifically defined, the mixing apparatus may be any one where a base can be dispersed in the cellulose-containing raw material. For example, there are mentioned various mixing machines such as a ribbon-type mixer, a paddle-type mixer, a conical planetary screw-type mixer, a kneader, etc.

Of those, more preferred is a horizontal screw-type paddle mixer, concretely a Ledige mixer that is a horizontal screw-type paddle mixer having chopper paddles.

After the cellulose-containing raw material having lowered crystallinity has been mixed with a base and water, the resulting mixture is preferably ripened from the viewpoint of increasing the speed of producing the alkali cellulose. The ripening temperature is preferably from 35 to 90° C., more preferably from 38 to 80° C., even more preferably from 40 to 70° C. The ripening time is preferably from 0.1 to 24 hours, more preferably from 0.5 to 12 hours, even more preferably from 1 to 6 hours.

The change from the cellulose-containing raw material to alkali cellulose can be confirmed through X-ray crystal diffractiometry.

(Hydroxypropylation of Alkali Cellulose)

Preferred embodiments of the amount of propylene oxide, the type of catalyst, the amount of catalyst and the reaction condition in hydroxypropylation of alkali cellulose are the same as those described in (hydroxypropylation) in the above-mentioned <(3-1-i) Production of C-HPC using cellulose-containing raw material having lowered crystallinity>.

(Cationization of Hydroxypropyl Cellulose)

Preferred embodiments of the type of the cationizing agent, the amount of the cationizing agent, the type of the catalyst, the amount of the catalyst and the reaction condition in cationization of hydroxypropyl cellulose are the same as those described in (cationization) in the above-mentioned <(3-1-i) Production of C-HPC using cellulose-containing raw material having lowered crystallinity>.

<(3-2-ii) Production of C-HPC Using Cellulose-Containing Raw Material Having High Crystallinity: Method (c)>

(Treatment of Cellulose-Containing Raw Material to Give Alkali Cellulose)

The cellulose-containing raw material is treated in a grinder along with a base and substantially with no water therein to give a ground cellulose/base mixture, which is then mixed with water to give an alkali cellulose.

Preferred embodiments of the type, the shape, the degree of crystallinity and the mean degree of polymerization of the cellulose-containing raw material are the same as those in the section of (cationization of high-crystalline cellulose-containing raw material) in the above-mentioned Method (a).

Preferred embodiments of the type of the base compound, and the amount of the base are the same as those in the section of (treatment into alkali cellulose) in the above-mentioned Method (b).

From the viewpoint of reducing the water content during grinding, preferably, the base is mixed with the cellulose material in the absence of water therein.

Preferably, the treatment in the grinder is carried out substantially in the absence of water therein. Specifically, from the viewpoint of improving the productivity such as the grinding efficiency and the easiness in water removal, the water content in the system is preferably at most 10% by mass relative to the cellulose-containing raw material, more preferably from 0.01 to 8% by mass, even more preferably from 0.1 to 6% by mass, further more preferably from 1 to 5% by mass.

Preferred embodiments of the type of the grinder and the grinding condition are the same as those described in the section of (production of cellulose-containing raw material having lowered crystallinity) in the above-mentioned <(3-1-i) Production of C-HPC using cellulose-containing raw material having lowered crystallinity>.

From the viewpoint of increasing the speed in producing alkali cellulose, from the viewpoint of increasing the yield of alkali cellulose, and from the viewpoint of preventing the mean degree of polymerization of cellulose from lowering, preferably, the cellulose/base mixture is ground so that the mean particle size of the cellulose in the ground cellulose/base mixture could be from 10 to 150 μm, more preferably from 20 to 130 μm, even more preferably from 40 to 100 μm, still more preferably from 50 to 80 μm. The mean particle size of the ground cellulose/base mixture may be determined according to the method described in the section of Examples.

From the viewpoint of increasing the yield of alkali cellulose, and from the viewpoint of enhancing the productivity of alkali cellulose with the cationizing agent and propylene oxide to be mentioned below, preferably, water is mixed with the ground cellulose/base mixture in such a manner that the water content in the ground cellulose/base mixture could be from 30 to 100% by mass relative to the cellulose in the cellulose-containing raw material, more preferably from 35 to 70% by mass, even more preferably from 40 to 60% by mass.

(Hydroxypropylation of Alkali Cellulose)

Preferred embodiments of the amount of propylene oxide, the type of the catalyst, the amount of the catalyst and the reaction condition in hydroxypropylation of alkali cellulose are the same as those described in the section of (hydroxypropylation) in the above-mentioned <(3-1-i) Production of C-HPC using cellulose-containing raw material having lowered crystallinity>.

(Cationization of Hydroxypropyl Cellulose)

Preferred embodiments of the type of the cationizing agent, the amount of the cationizing agent, the type of the catalyst, the amount of the catalyst and the reaction condition in cationizing hydroxypropyl cellulose are the same as those described in the section of (cationization) in the above-mentioned <(3-1-i) Production of C-HPC using cellulose-containing raw material having lowered crystallinity>.

The reaction sequence of the hydroxypropylation and the cationization in the above-mentioned methods (b) and (c) may be transposed, but from the viewpoint of increasing the degree of substitution with cationized ethyleneoxy group, the reaction order is the hydroxypropylation first followed by the cationization.

The production method for C-HPC for use in the present invention is preferably the method (method (a) mentioned below) of <(3-1-ii) Production of C-HPC using cellulose-containing raw material having high crystallinity, for example, pulp> in the above-mentioned method (3-1), or the method (method (b) or (c) mentioned below) described in (3-2), from the viewpoint of good finger combability, body and manageability of the hair treated with the hair treatment composition of the present invention and dried.

Concretely, C-HPC is preferably one obtained according to the method including the following steps (a-1) to (a-3), or the method including the following step (a-4) and (a-5), or the method including the following steps (b-1) to (b-4), or the method including the following steps (c-1) to (c-4), from the viewpoint of good finger combability, body and manageability of the hair treated with the hair treatment composition of the present invention and dried, and is more preferably one obtained according to the method including the steps (a-1) to (a-3), or one obtained according to the method including the steps (b-1) to (b-4), or one obtained according to the method including the steps (c-1) to (c-4).

Method (a):

Step (a-1): a step of adding a cationizing agent to a cellulose-containing raw material and processing it with a grinder.

Step (a-2): a step of adding a base to the grinder-processed product obtained in the step (a-1), and while processing it with a grinder, reacting the cellulose-containing raw material and the cationizing agent to give a cationized cellulose.

Step (a-3): a step of reacting the cationized cellulose obtained in the step (a-2) with propylene oxide to give a cationized hydroxypropyl cellulose (A).

Step (a-4): a step of adding a base to a cellulose-containing raw material and processing it with a grinder for crystallinity reduction, and thereafter while a cationizing agent is added thereto and processing it with a grinder for crystallinity reduction, reacting the cellulose-containing raw material and the cationizing agent to give a cationized cellulose.

Step (a-5): a step of reacting the cationized cellulose obtained in the step (a-4) with propylene oxide to give a cationized hydroxypropyl cellulose.

Method (b):

Step (b-1): a step of processing a cellulose-containing raw material with a grinder to give a cellulose-containing raw material that contains a cellulose having a degree of crystallinity of from 10 to 50%.

Step (b-2): a step of adding to the cellulose-containing raw material obtained in the step (b-1), a base in an amount of from 0.6 to 1.5 molar times per mol of AGU that constitutes the cellulose in the cellulose-containing raw material, and water in an amount of from 20 to 100% by mass relative to the cellulose in the cellulose-containing raw material, thereby giving an alkali cellulose.

Step (b-3): a step of reacting the alkali cellulose obtained in the step (b-2) and propylene oxide to give a hydroxypropyl cellulose.

Step (b-4): a step of reacting the hydroxypropyl cellulose obtained in the step (b-3) with a cationizing agent to give the cationized hydroxypropyl cellulose (A).

Method (c):

Step (c-1): a step of processing a mixture of a cellulose-containing raw material and a base in an amount of from 0.6 to 1.5 molar times per mol of AGU that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm.

Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose.

Step (c-3): a step of reacting the alkali cellulose obtained in the step (c-2) with propylene oxide to give a hydroxypropyl cellulose.

Step (c-4): a step of reacting the hydroxypropyl cellulose obtained in the step (c-3) with a cationizing agent to give a cationized hydroxypropyl cellulose (A).

(Content of C-HPC)

The content of C-HPC for use in the present invention is, from the viewpoint of good finger combability, body and manageability of the hair treated with the hair treatment composition of the present invention and dried, preferably at least 0.005% by mass in the hair treatment composition, more preferably at least 0.01% by mass, even more preferably at least 0.05% by mass, further more preferably at least 0.2% by mass. From the viewpoint of good finger combability and body of the hair treated with the hair treatment composition and dried and from the viewpoint of reducing the viscosity of the hair treatment composition, the content is preferably at most 20% by mass, more preferably at most 15% by mass, even more preferably at most 10% by mass, further more preferably at most 7% by mass.

Summing up these viewpoints, the content of C-HPC is preferably from 0.005 to 20% by mass in the hair treatment composition, more preferably from 0.01 to 15% by mass, even more preferably from 0.05 to 10% by mass, further more preferably from 0.2 to 7% by mass.

In case where the hair treatment composition is a multi-pack hair treatment composition such as a two-pack hair treatment or a two-pack permanent wave agent to be mentioned below, the above-mentioned content is the content in the first pack or the second pack of the composition.

[Hair Treatment Composition]

The hair treatment composition of the present invention contains at least one treating agent (B) selected from a hair-coloring dye, an oxidizing agent, an alkali agent and a keratin-reducing agent, in addition to C-HPC.

The hair treatment composition of the present invention means a treatment composition in the broad sense of the term, including general concepts of hair color, hair bleach, permanent wave agent, straight perm agent, sustainable hair set agent, hair relaxer, etc.

Typical embodiments of the hair treatment composition of the present invention include hair color and perm agent. Hereinunder "hair color" has a concept of including a dye-including hair color and a dye-free hair bleach, and includes an agent that bleaches and colors hair.

The hair color includes, for example, a one-pack hair color of the following (a) and (b), and a multi-pack hair color of the following (c) and (d).

(a) One-pack hair color containing a hair-coloring dye and optionally an oxidizing agent.

(b) One-pack hair color not containing a hair-coloring dye but containing an oxidizing agent.

(c) Two-pack hair color composed of a first pack containing an alkali agent and/or hair-coloring dye, and a second pack containing an oxidizing agent.

(d) Three-pack hair color composed of a first pack containing an alkali agent and/or a hair-coloring dye, a second pack containing an oxidizing agent, and a third pack containing an oxidation promoter.

"Perm agent" is a concept including a permanent wave agent, a straight perm agent and a hair relaxer, and is a two-pack agent composed of a first agent that contains a keratin-reducing agent and a second agent that contains an oxidizing agent.

As in the above, the hair treatment composition of the present invention contains at least one treating agent (B) selected from a hair-coloring agent, an oxidizing agent, an alkali agent and a keratin-reducing agent, besides C-HPC.

<Hair Color>

The hair color contains at least one treating agent (B) selected from a hair-coloring dye, an oxidizing agent and an alkali agent, in addition to C-HPC.

(Hair-Coloring Dye)

The hair-coloring dye includes a direct dye and an oxidation dye intermediate.

Not specifically defined, the direct dye may be any one generally usable in cosmetics and others, including a nitro dye, an anthraquinone dye, an acid dye, an oil-soluble dye, a basic dye, etc.

The nitro dye includes HC Blue 2, HC Orange 1, HC Red 1, HC Red 3, HC Yellow 2, HC Yellow 4, etc. The anthraquinone dye includes 1-amino-4-methylaminoanthraquinone, 1,4-diaminoanthraquinone, etc.

The acid dye includes Red series, Orange series, Yellow series, Green series, Blue series, Violet 401, Black 401, Acid Blue 1, 3, 62, Acid Black 52, Acid Brown 13, Acid Green 50, Acid Orange 6, Acid Red 14, 35, 73, 184, Brilliant Black 1, etc.

The oil-soluble dye includes Red series, Orange series, Yellow series, Green 202, Violet 201, Blue 403, etc. The basic dye includes Basic Blue 6, 7, 9, 26, 41, 99, Basic Brown 4, 16, Basic Brown 17, Basic Green 1, Basic Red 2, 12, 22, 51, 76, Basic Violet 1, 3, 10, 14, 57, Basic Yellow 57, 87, Basic Orange 31, etc.

As the oxidation dye intermediate, usable here are known precursors and couplers generally used in hair color.

The precursor includes paraphenylenediamine, toluene-2,5-diamine, orthochloroparaphenylenediamine, N-phenylparaphenylenedimaine, N, N-bis(hydroxyethyl) paraphenylenediamine, 3-methyl-4-aminophenol, 2-hydroxyethylparaphenylenediamine, para-aminophenol, paramethylaminophenol, 4-aminometacresol, orthoaminophenol, and their salts, etc. The coupler includes resorcinol, 2-methylresorcinol, 1-naphthol, 1,5-dihydroxynaphthalene, 5-aminoorthocresol, metaphenylenediamine, metaaminophenol, 2,4-diaminophenoxyethanol, 2,6-diaminopyridine, 2-methyl-5-hydroxyethylaminophenol, 2-amino-3-hydroxypyridine, and their salts, etc.

(Oxidizing Agent)

The oxidizing agent includes hydrogen peroxide, urea peroxide that is a generator of hydrogen peroxide or oxygen, melamine peroxide, sodium perborate, potassium perborate, sodium percarbonate, potassium percarbonate, etc. From the viewpoint of the hair-coloring capability thereof, preferred is hydrogen peroxide.

(Oxidation Promoter)

The oxidation promoter includes, for example, persulfates, etc. Concretely there are mentioned ammonium persulfate, potassium persulfate, sodium persulfate, etc. Preferably, these are in a powdery form such as granules.

(Alkali Agent)

The alkali agent includes ammonia and its salts; alkanolamines such as monoethanolamine, isopropanolamine, 2-amino-2-methylpropanol, 2-aminobutanol and the like, and their salts; alkanediamines such 1,3-propanediamine and the like, and their salts; carbonates such as guanidine carbonate, sodium carbonate, potassium carbonate, sodium hydrogencarbonate, potassium hydrogencarbonate, etc. Of those, more preferred are ammonia, alkanolamines and their salts from the viewpoint of the hair-coloring capability thereof.

One alone or two or more different types of the above-mentioned direct dyes, oxidation dye intermediates, oxidizing agents, oxidation promoters and alkali agents may be used here either singly or as combined.

The content of the direct dye is preferably from 0.005 to 5% by mass in the hair treatment composition.

The content of the precursor and the coupler as the oxidation dye intermediate is each preferably from 0.01 to 10% by mass, more preferably from 0.1 to 5% by mass, from the viewpoint of the hair-coloring capability thereof.

The content of the oxidizing agent is preferably from 0.1 to 12% by mass, more preferably from 0.5 to 9% by mass in the hair treatment composition, from the viewpoint of sufficient hair-coloring or bleaching capability and from the viewpoint of reducing hair damage or head skin irritation.

The content of the oxidation promoter is preferably from 0.1 to 50% by mass, more preferably from 1 to 30% by mass, even more preferably from 3 to 25% by mass in the hair-treatment composition, from the viewpoint of sufficient bleaching capability and from the viewpoint of reducing hair damage or head skin irritation.

The content of the alkali agent is preferably from 0.1 to 10% by mass in the hair treatment composition from the viewpoint of sufficient hair-coloring or bleaching capability and from the viewpoint of reducing hair damage or head skin irritation.

The pH of the hair color is preferably from 3 to 9 for a one-pack hair color for preventing damage of skin and hair. Of a two-pack hair color, the pH of the first pack is preferably from 8 to 13 and that of the second pack is preferably from 2 to 5. Of a three-pack hair color, the pH of the first pack is preferably from 8 to 13 and that of the second pack is preferably from 2 to 5. The pH control can be attained by using a known pH regulator.

Regarding the type thereof, the present invention is applicable to any type of hair color, including one for use at room temperature, one for use under heat, etc.

In the two-pack hair color, the content ratio (by mass) of the first pack to the second pack [first pack/second pack] is preferably from 2/8 to 6/4, more preferably from 3/7 to 5/5, even more preferably from 3.5/6.5 to 4.5/5.5.

<Perm Agent>

The perm agent includes a keratin-reducing agent, an alkali agent and an oxidizing agent as the treating agent (B), in addition to C-HPC.

(Keratin-Reducing Agent)

The keratin-reducing agent can cleave the disulfide bonds of keratin that constitutes hair. The hair treatment composition containing such a keratin-reducing agent is favorably used as the first pack of a permanent wave agent.

The keratin-reducing agent includes thioglycolic acid and its derivatives, thiolactic acid and its derivatives, cysteine and its derivatives, and their salts, as well as thioglyceryl alkyl ethers of the following formula (4) and their salts, and mercaptoalkylamides of the following formula (5) and their salts, etc.

$$R^7OCH_2CH(OH)CH_2SH \quad (4)$$

(In the formula, $R^7$ represents a hydrogen atom, a lower alkyl group or a lower alkoxy-lower alkyl group.)

$$H\text{---}(CHOH)_x\text{---}(CH_2)_y\text{---}CONH(CH_2)_z\text{---}SH \quad (5)$$

(In the formula, x indicates a number of from 0 to 5, y indicates a number of from 0 to 3, z indicates a number of from 2 to 5; however, y and z are not 0 at the same time.)

Specific examples of the keratin-reducing agent include thioglycolic acid, glyceryl thioglycolate; L-cysteine, D-cysteine, N-acetylcysteine, and ammonium salts of those cysteines, and ethanolamine salts of those cysteines such as monoethanolamine, diethanolamine, triethanolamine and the like; thioglyceryl alkyl ethers such as ethoxyhydroxypropanethiol, methoxyethoxyhydroxypropanethiol, isopropoxyethoxyhydroxypropanethiol, etc.; mercaptoethylpropanamide, mercaptoethylgluconamide, etc.

The content of the reducing agent is preferably from 0.1 to 20% by mass, more preferably from 1 to 15% by mass, even more preferably from 1 to 10% by mass in the hair treatment composition, from the viewpoint of cleaving the disulfide bonds of keratin that constitutes hair thereby attaining well-finished permanent wave.

(Alkali Agent)

The alkali agent is used along with the keratin-reducing agent.

The alkali agent may be the same as that mentioned hereinabove for hair color. Above all, preferred are ammonia, alkanolamines and their salts and sodium hydrogencarbonate, from the viewpoint of enhancing the action of the keratin-reducing agent.

(Oxidizing Agent)

The oxidizing agent is incorporated in the second pack of a permanent wave agent to be combined with the first pack thereof. The oxidizing agent includes potassium bromate, sodium bromate, sodium perborate, hydrogen peroxide, etc.

The content of the oxidizing agent is preferably from 1 to 20% by mass, more preferably from 2 to 10% by mass in the hair treatment composition. With that, the disulfide bonds of keratin cut in hair can be fully recombined.

The pH of the perm agent is preferably from 6 to 12 for the first pack and from 3 to 9 for the second pack, for preventing damage of skin and hair. The pH control can be attained by using a known pH regulator.

Regarding the type thereof, the present invention is applicable to any type of hair agents, including those for use at room temperature, those for use under heat, those for wave formation, those for hair relaxation, etc.

In the two-pack permanent wave agent, the content ratio (by mass) of the first pack to the second pack [first pack/second pack] is preferably from 3/7 to 7/3, more preferably from 4/6 to 6/4, even more preferably from 4.5/5.5 to 5.5/4.5.

<Other Components>

The hair treatment composition of the present invention contains the above-mentioned C-HPC and at least one treating agent (B) selected from a hair-coloring dye, an oxidizing agent, an alkali agent and a keratin-reducing agent, and may contain any other component generally used as cosmetic materials, in addition to the above. The optional components include a feel improver, a thickener, a surfactant, an oil, a fragrance, a UV absorbent, a visible light absorbent, a chelating agent, an antioxidant, a colorant, a preservative, a pH regulator, a viscosity regulator, a pearly gloss agent, a moisturizer, etc.

(Feel Improver, Thickener)

As the feel improver and the thickener, there are mentioned protein hydrolyzates such as typically water-soluble collagen and collagen derivatives; cationic polymers such as cationic group-containing copolymers described in Japanese Patent 3472491, cationized guar gum derivatives described in JP-B 58-35640, 60-46158 and JP-A 58-53996, cationized hydroxyethyl cellulose described in JP-A 4-108723, LUVIQUAT SENSATION sold by BASF; MARCOAT 100, 550 and others sold by Nalco; anionic polymers such as carboxyvinyl polymer, etc.; ampholytic polymers; other water-soluble polymers such as hydroxyethyl cellulose, hydroxypropyl cellulose, polyethylene glycol, etc.

(Surfactant)

The hair treatment composition of the present invention preferably contains at least one surfactant selected from anionic surfactants, ampholytic surfactants, nonionic surfactants and cationic surfactants. Not specifically defined, the surfactant may be any one generally used in medicines, quasi-drugs, cosmetics, toiletries and others, including anionic surfactants, nonionic surfactants, ampholytic surfactants and cationic surfactants.

Specific examples of the anionic surfactant includes (i) sulfate ester salts such as alkyl sulfate salts, alkenyl sulfate salts, polyoxyalkylene alkyl ether sulfate salts, polyoxyalkylene alkenyl ether sulfate salts, polyoxyalkylene alkylphenyl ether sulfate salts, etc.; (ii) sulfonate salts such as acylisethionates, acylmethyltaurates, alkyl sulfonates, alkyl sulfosuccinates salts, polyoxyalkylene alkyl sulfosuccinate salts, etc.; (iii) amino acid salts such as acylglutamic acid salts, alanine derivatives, glycine derivatives, arginine derivatives, etc.; (iv) carboxylic acid salts such as higher fatty acid salts, polyoxyalkylene alkylether acetate salts, etc.; (v) phosphate salts such as alkyl phosphate salts, polyoxyalkylene alkyl ether phosphate salts, etc.

The nonionic surfactant includes polyalkylene glycol-type surfactants such as polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hardened) castor oil, etc.; polyalcohol-type surfactants such as sucrose fatty acid esters, polyglycerin alkyl ethers, polyglycerin fatty acid esters, alkyl glycosides, etc.; and fatty acid alkanolamides.

The ampholytic surfactant includes betaine-type surfactants and amine oxide-type surfactants. Concretely, there are mentioned betaine-type surfactants such as imidazoline betaines, alkyldimethylaminoacetate betaines, fatty acid amide propylbetaines, sulfobetaines, etc.; and amine oxide-type surfactants such as alkyldimethylamine oxides, etc.

The cationic surfactant includes salts of mineral acids or organic acids with tertiary amines represented by the following formula (6), and quaternary ammonium-type surfactants represented by the following formula (7).

(In the formula, $R^{15}$ represents a linear or branched alkyl or alkenyl group having from 6 to 28 carbon atoms and optionally interrupted by an amide group, an ester group or an ether group; $R^{16}$ represents a linear or branched alkyl, alkenyl or alkanol group having from 1 to 28 carbon atoms and optionally interrupted by an amide group, an ester group or an ether group; $R^{17}$ represents a linear or branched alkyl or alkanol group having from 1 to 3 carbon atoms.)

(In the formula, $R^{18}$ represents a linear or branched alkyl or alkenyl group having from 6 to 28 carbon atoms and optionally interrupted by an amide group, an ester group or an ether group; $R^{19}$ represents a linear or branched alkyl, alkenyl or alkanol group having from 1 to 28 carbon atoms and optionally interrupted by an amide group, an ester group or an ether group; $R^{20}$ and $R^{21}$ each represent a linear or branched alkyl group having from 1 to 3 carbon atoms; $Z^-$ represents an anion group or a counter ion to the ammonium salt.)

The mineral acid or the organic acid to form a salt with the tertiary amine represented by the above-mentioned formula (6) is not specifically defined, but from the viewpoint of dispersion stability of the surfactant, preferred are hydrogen halides, sulfuric acid, acetic acid, citric acid, lactic acid and alkylsulfuric acids having from 1 to 3 carbon atoms. As the hydrogen halide, preferred is hydrogen chloride from the viewpoint of chemical stability.

Specific examples of the cationic surfactants represented by the above-mentioned formula (6) or (7) include mono-long-chain alkyltrimethylammonium chlorides such as stearyltrimethylammonium chloride, behenyltrimethylammonium chloride, stearoxypropyltrimethylammonium chloride, etc.; di-long-chain alkyldimethylammonium chlorides such as distearyldimethylammonium chloride, diisostearyldimethylammonium chloride, etc.; glutamates, hydrochlorides, citrates or lactates of mono-long chain dimethylamines or mono-long chain diethylamines such as stearyldimethylamine, behenyldimethylamine, octadecyloxypropyldimethylamine, stearamidethyldiethylamine, stearamidopropyldimethylamine, behenamidopropyldimethylamine, etc.

In the hair treatment composition of the present invention, the content of the surfactant is preferably from 0.1 to 50% by mass, preferably from 0.3 to 40% by mass, more preferably from 0.5 to 30% by mass, from the viewpoint of the finger combability, body and manageability of the hair treated with the hair treatment composition and dried and from the viewpoint of viscosity control of the composition.

[Oil]

The hair treatment composition of the present invention preferably contains an oil from the viewpoint of improving the good finger combability and manageability of the hair treated with the hair treatment composition and dried.

Not specifically defined, the oil may be any one generally usable in medicines, quasi-drugs, cosmetics, toiletries, etc. Concretely, there are mentioned higher alcohols, silicones, ether oils, ester oils, hydrocarbons, glycerides, vegetable oils, animal oils, lanoline derivatives, higher fatty acid esters, etc.

The higher alcohol includes 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyldodecanol, eicosyl alcohol, behenyl alcohol.

The silicone includes, described as in JP-A 6-48916, (a) dimethylpolysiloxane, (b) methylphenylpolysiloxane, (c) amino-modified silicones [as aqueous suspension, there are mentioned SM8704C (by Toray Dow Corning), DC939 (by Toray Dow Corning), etc.], (d) fatty acid-modified polysiloxanes, (e) alcohol-modified silicones, (f) aliphatic alcohol-modified polysiloxanes, (g) polyether-modified silicones, (h) epoxy-modified silicones, (i) fluorine-modified silicones, (j) cyclic silicones, (k) alkyl-modified silicones, (l) amino-modified siloxane-polyoxyalkylene block copolymers, etc.

The ether oil includes polyoxypropylene hexyl ether, polyoxypropylene octyl ether, polyoxypropylene 2-ethylhexyl ether, polyoxypropylene decyl ether, polyoxypropylene lauryl ether, polyoxypropylene myristyl ether, polyoxypropylene cetyl ether, and polyoxypropylene stearyl ether, in which the mean addition molar number of the propyleneoxy groups is from 3 to 15; dihexyl ether, dioctyl ether, didecyl ether, dilauryl ether, dimyristyl ether, dicetyl ether, distearyl ether, diicosyl ether, dibehenyl ether, etc.

The ester oil is preferably a monoester oil or an ester oil having at least two ester bonds in the molecule, or a mixture of two or more of such ester oils.

Specific examples of the ester oil include vegetable oils such as castor oil, cacao oil, mink oil, avocado oil, olive oil, sunflower oil, camellia oil, macadamia nut oil, shea butter oil, etc.; synthetic ester oils such as dioctyl carbonate, polyoxypropylene (mean addition molar number 3) benzyl ether citrate, polyoxypropylene (mean addition molar number 3) benzyl ether myristate, polyoxypropylene (mean addition molar number 3) benzyl ether 2-ethylhexanoate, etc.

The hydrocarbon oil includes squalene, squalane, liquid paraffin, liquid isoparaffin, heavy liquid isoparaffin, α-olefin oligomer, cycloparaffin, polybutene, vaseline, paraffin, microcrystalline wax, polyethylene wax, ceresin, etc.

From the viewpoint of good finger combability and manageability of the hair treated with the hair treatment composition and dried and from the viewpoint of emulsification stability, the oil content in the hair treatment composition is preferably from 1 to 30% by mass, more preferably from 1.5 to 25% by mass, even more preferably from 2 to 20% by mass.

The hair cosmetic of the present invention can be produced according to an ordinary method. The forms of the composition are not specifically defined. The composition can be in any form of liquid, foam, paste, cream, solid, powder, etc. Preferred is liquid, paste or cream; and more preferred is liquid.

In case where the composition is liquid, water, polyethylene glycol, ethanol or the like is preferably used as the liquid medium, and the water content in the composition is preferably from 10 to 90% by mass of the entire composition.

[Method for Producing Hair Treatment Composition]

The method for producing the hair treatment composition of the present invention is a method for producing the hair treatment composition containing a cationized hydroxypropyl cellulose (A) and at least one treating agent (B) selected from a hair-coloring dye, an oxidizing agent, an alkali agent and a keratin-reducing agent, and the method includes the above-mentioned steps (a-1) to (a-3), the above-mentioned steps (a-4) to (a-5), the above-mentioned steps (b-1) to (b-4), or the above-mentioned steps (c-1) to (c-4).

From the viewpoint of good finger combability, body and manageability of the hair treated with the hair treatment composition and dried, the production method of the invention preferably comprises the above-mentioned steps (a-1) to (a-3), the above-mentioned steps (b-1) to (b-4), or the above-mentioned steps (c-1) to (c-4). Further from the viewpoint of preventing the reduction in the molecular weight of C-HPC, more preferably, the method comprises the above-mentioned steps (b-1) to (b-4), or the above-mentioned steps (c-1) to (c-4).

Relative to the above-mentioned embodiments, the present invention discloses the following hair treatment composition and the following production method for the composition.

[1] A hair treatment composition containing a cationized hydroxypropyl cellulose (A) and at least one treating agent (B) selected from a hair-coloring dye, an oxidizing agent, an alkali agent and a keratin-reducing agent.

[2] The hair treatment composition according to the above [1], wherein the cationized hydroxypropyl cellulose (A) has an anhydroglucose-derived main chain represented by the following general formula (1), and has a degree of substitution with cationized ethyleneoxy group of from 0.01 to 2.9, preferably from 0.1 to 2.5, more preferably from 0.2 to 2.0, even more preferably from 0.3 to 1.5, further more preferably from 0.8 to 1.2, and a degree of substitution with propyleneoxy group of from 0.1 to 4.0, preferably from 0.2 to 3.0, more preferably from 0.3 to 2.8, even more preferably from 0.6 to 2.5, further more preferably from 1.0 to 2.0:

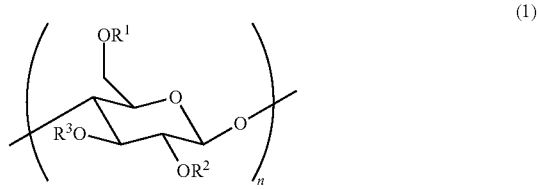

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 50 to 5000, preferably from 200 to 2000, more preferably from 300 to 1500, even more preferably from 400 to 1000.)

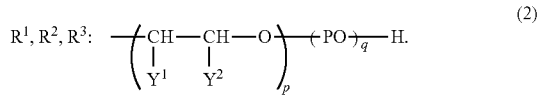

(In the formula, one of $Y^1$ and $Y^2$ is a hydrogen atom and the other is a cationic group represented by the following general formula (3); PO represents a propyleneoxy group; p indicates the number of cationized ethyleneoxy groups $((-CH(Y^1)-CH(Y^2)-O-)$ in the general formula (2) and q indicates the number of propyleneoxy groups (—PO—) therein, each being 0 or a positive integer, preferably an integer of from 0 to 2, more preferably 0 or 1; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer.)

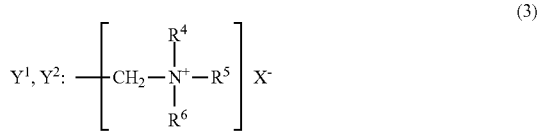

(In the formula, $R^4$, $R^5$ and $R^6$ each independently represent a linear or branched alkyl group having from 1 to 3 carbon atoms, preferably a methyl group or an ethyl group, more preferably a methyl group. $X^-$ represents an anionic group, preferably a halide ion).

[3] The hair treatment composition according to the above [1] or [2], wherein the content of the cationized hydroxypropyl cellulose (A) is from 0.001 to 20% by mass, preferably from 0.005 to 20% by mass, more preferably from 0.01 to 15% by mass, even more preferably from 0.05 to 10% by mass, further more preferably from 0.2 to 7% by mass.

[4] The hair treatment composition according to any of the above [1] to [3], wherein the mean degree of polymerization of anhydroglucose is a number of from 400 to 1000.

[5] The hair treatment composition according to any of the above [1] to [4], wherein the oxidizing agent is hydrogen peroxide.

[6] The hair treatment composition according to any of the above [1] to [5], wherein the alkali agent is at least one selected from a group consisting of ammonia, alkanolamines and their salts.

[7] The hair treatment composition according to any of the above [1] to [6], wherein the keratin-reducing agent is at least one selected from a group consisting of thioglycolic acid and its derivatives, thiolactic acid and its derivatives, cysteine and its derivatives, thioglyceryl alkyl ethers of the following formula (4), mercaptoalkylamides of the following formula (5), and their salts.

(In the formula, $R^7$ represents a hydrogen atom, a lower alkyl group or a lower alkoxy-lower alkyl group.)

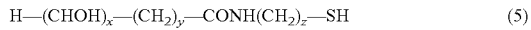

(In the formula, x indicates a number of from 0 to 5, y indicates a number of from 0 to 3, z indicates a number of from 2 to 5; however, y and z are not 0 at the same time.)

[8] The hair treatment composition according to any of the above [1] to [7], wherein the cationized hydroxypropyl cellulose (A) is obtained by the following steps (a-1) to (a-3):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A).

[9] The hair treatment composition according to any of the above [1] to [7], wherein the cationized hydroxypropyl cellulose (A) is obtained by the following steps (b-1) to (b-4):

Step (b-1): a step of processing a cellulose-containing raw material with a grinder to give a cellulose-containing raw material that contains a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) and propylene oxide to give a hydroxypropyl cellulose, Step (b-4): a step of reacting the hydroxypropyl cellulose obtained in the step (b-3) with a cationizing agent to give the cationized hydroxypropyl cellulose (A).

[10] The hair treatment composition according to any of the above [1] to [7], wherein the cationized hydroxypropyl cellulose (A) is obtained by the following steps (c-1) to (c-4):

Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

[11] A method for producing a hair treatment composition containing a cationized hydroxypropyl cellulose (A) and at least one treating agent (B) selected from a hair-coloring dye, an oxidizing agent, an alkali agent and a keratin-reducing agent; the method including the steps (a-1) to (a-3) stated in the above [8], the steps (b-1) to (b-4) stated in the above [9], or the steps (c-1) to (c-4) stated in the above [10].

[12] Use of the composition stated in the above [1] to [7] as a hair treatment agent.

[13] Use according to the above [12], wherein the hair treatment agent is a hair color.

[14] Use according to the above [12], wherein the hair treatment agent is a perm agent.

EXAMPLES

Unless otherwise specifically indicated in the following Examples and Comparative Examples, "part" is "part by mass" and "%" is "% by mass".

Measurement methods for the physical properties of the samples in Examples and Comparative Examples are as described below.

(1) Calculation of Crystallinity of Pulp and Powdery Cellulose

Using Rigaku's "Rigaku RINT 2500VC X-RAY Diffractometer", the sample was analyzed under the condition mentioned below, and from the peak intensity on the diffraction spectrum, the degree of crystallinity of the sample was calculated according to the above-mentioned math formula (1).

X-ray source: Cu/Kα-radiation, bulb voltage: 40 kV, bulb current: 120 mA

Detection range: 2κ=5 to 45°

Sample: prepared by compressing a pellet having an area of 320 mm$^2$ and a thickness of 1 mm X-ray scanning speed: 10°/min In case where the degree of crystallinity thus measured was a negative value, all such samples were considered to have a crystallinity of 0%.

(2) Measurement of Mean Particle Size of Cellulose in Powdery Cellulose, and Ground Cellulose/Base Mixture The mean particle size of powdery cellulose was determined, using a laser diffraction/scattering particle sizer "LA-920" (by Horiba). The test sample was prepared by adding 0.1 g of a powdery cellulose to 5 mL of water and ultrasonicated for 1 minute to prepare a sample dispersion. The volume-based median diameter was measured at a temperature of 25° C., and was referred to as the mean particle size.

The mean particle size of cellulose in a ground cellulose/base mixture was determined using the same apparatus. Ethanol was added to a ground cellulose/base mixture and the concentration of the resulting mixture was so controlled that the transmittance thereof could fall within a range of from 70 to 95%. The mixture was ultrasonicated for 1 minute, and NaOH was added thereto to prepare a sample dispersion.

(3) Measurement of Water Content in Pulp and Powdery Cellulose

The water content in pulp or powdery cellulose was measured, using an IR moisture meter (Kett Electric Laboratory's "FD-610"). The measurement temperature was 120° C., and the point at which the weight change for 30 seconds reached at most 0.1% was referred to as the final point in the measurement.

(4) Calculation of Substitution Degree in C-HPC

C-HPC produced in Production Example was purified through a dialytic membrane (molecular weight cut off, 1000), and then the aqueous solution was freeze-dried to give a purified C-HPC. The chlorine content in the thus-obtained pure C-HPC was measured through elementary analysis. The number of the cationic groups contained in C-HPC and the number of the chloride ions that are counter ions were approximated to be the same number, and the amount of the cationized ethyleneoxy groups (—CH(Y$^1$)—CH(Y$^2$)O—) contained in the unit mass of C-HPC (a (mol/g)) was calculated according to the following math formula (2).

$$a \text{ (mol/g)} = \text{chlorine content (\%) obtained through elementary analysis}/(35.5 \times 100) \quad (2)$$

The hydroxypropoxy group content (%) was determined according to the "Method for Analysis of Hydroxypropyl Cellulose" described in Japanese Pharmacopoeia, except that the object to be analyzed here was pure C-HPC but not hydroxypropyl cellulose. According to the math formula (3) mentioned below, the hydroxypropoxy group content [formula weight (OC$_3$H$_6$OH=75.09)] (b mol/g) was obtained.

$$b \text{ (mol/g)} = \text{hydroxypropoxy group content (\%) obtained through gas chromatography}/(75.09 \times 100) \quad (3)$$

From the thus-obtained a and b and according to the following math formulae (4) and (5), the degree of substitution with cationized ethyleneoxy group (k) and the degree of substitution with propyleneoxy group (m) were calculated.

$$a = k/(162 + k \times K + m \times 58) \quad (4)$$

$$b = m/(162 + k \times K + m \times 58) \quad (5)$$

[In the formulae, k and K each indicate the degree of substitution with cationized ethyleneoxy group and the formula weight; and m indicates the degree of substitution with propyleneoxy group.]

(5) Measurement of Mean Degree of Polymerization (Copper ammonia method)

(5-1) Measurement of Viscosity-Average Degree of Polymerization of Pulp and Powdery Cellulose (i) Preparation of Solution for Measurement 0.5 g of cuprous chloride and 20 to 30 mL of aqueous 25% ammonia were put into a measuring flask (100 mL) and completely dissolved, and then 1.0 g of cupric hydroxide and aqueous 25% ammonia were added thereto to be an amount just before the gauge line. This was stirred for 30 to 40 minutes and completely dissolved. Subsequently, cellulose as accurately weighed was added thereto, and the above-mentioned aqueous ammonia was added thereto up to the gauge line. This was airtightly sealed up, and stirred with a magnetic stirrer for 12 hours for dissolution to thereby prepare a solution for measurement. The amount of the cellulose to be added was varied within a range of from 20 to 500 mg, and solutions for measurement each having a different concentration were prepared.

(II) Measurement of Viscosity-Average Degree of Polymerization

The solution for measurement (copper ammonia solution) obtained in the above (i) was put into an Ubbelohde viscometer and statically left in a thermostat chamber (20±0.1° C.) for 1 hour, and thereafter the flowing-down speed of the liquid was measured. From the flowing-down time (t (sec)) of the copper ammonia solution having a different cellulose concentration (g/dL) and the flowing-down time (t$_0$ (sec)) of a cellulose-free aqueous copper ammonia solution, the relative viscosity η$_r$ of each sample was determined according to the following formula:

$$\eta_r = t/t_0$$

Next, the reduced viscosity (η$_{sp}$/c) at each concentration was determined according to the following formula:

$$\eta_{sp}/c = (\eta_r - 1)/c$$

(c: cellulose concentration (g/dL))

Further, the reduced viscosity was extrapolated into c=0 to determine the intrinsic viscosity [η] (dL/g), and according to the following formula, the viscosity-average degree of polymerization (DP) was obtained.

DP=2000×[η]

(5-2) Measurement of Viscosity-Average Degree of Polymerization of C-HPC
(iii) Preparation of Solution for Measurement The solution for measurement was prepared in the same manner as that for the solution for measurement in the above (i), except that a pure C-HPC was used in place of the pure cellulose.
(Iv) Measurement of Viscosity-Average Degree of Polymerization The viscosity-average degree of polymerization was measured in the same manner as that for the solution for the viscosity-average degree of polymerization of the above (ii), except that a cellulose-equivalent concentration (g/dL) was used in place of the concentration of the measurement solution.

The cellulose-equivalent concentration ($C_{cell}$) means the mass (g) of the cellulose skeleton part contained in 1 dL of the measurement solution, and is defined by the following math formula (6).

$$C_{cell}=u\times 162/(162+k\times K+m\times 58) \quad (6)$$

[In the formula, u indicates the mass (g) of C-HPC that had been accurately weighed in preparation of the measurement solution; and k, K and m have the same meanings as in the above-mentioned math formulae (4) and (5).]
(6) Measurement of 2% Viscosity With stirring, C-HPC was added to water having a temperature of 25° C. to prepare an aqueous 2 mass % C-HPC solution. This was put into a viscometer tube with careful attention thereto so that no bubble could come therein, and sealed up with a parafilm, and statically left in a water bath at 30° C. for about 1 hour. Next, a rotor (No. M1 to M4) and a rotation number (6 to 60 rpm) were selected in accordance with the viscosity of the sample, and using a B-type viscometer (Toki Sangyo's Model TVB-10), the value indicated by the viscometer when the rotor was rotated for 1 minute was read out, and the viscosity was thereby calculated.

Production Example 1

Production of C-HPC (1)

(1) Chipping Step

A sheet-like wood pulp (Tembec's Biofloc HV+, having a mean degree of polymerization of 1770, a degree of crystallinity of 74% and a water content of 7.0%) was pelletized with a sheet pelletizer (Horai's "SGG-220")) into chips of from 3 to 5 mm square.
(2) Cationization Step (1)

23.4 g of an aqueous solution of glycidyltrimethylammonium chloride (by Sakamoto Chemical Industry, water content 20%, purity 90% or more) (hereinafter referred to as "GMAC") (the amount corresponds to 0.2 mols per mol of AGU of cellulose) was added to 100 g of the chip-like pulp obtained in the above (1), and mixed in a mortar, and then put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%). This was ground for 30 minutes (frequency 20 Hz, vibrational amplitude 8 mm, temperature 30 to 70° C.) thereby giving a powdery mixture of cellulose and GMAC.

20 g (corresponding to 0.2 mols per mol of AGU) of an aqueous 24.7% sodium hydroxide solution was added to the obtained powdery mixture, mixed in a mortar and put into the above-mentioned batch-type vibrational mill. Under the same condition as above, this was ground for 60 minutes to give 151 g of a cationized cellulose (i).
(3) Cationization Step (2)

128 g of the cationized cellulose (i) obtained in the above (2) was mixed with 31.3 g of GMAC (corresponding to 0.32 mols per mol of AGU) in a mortar, and then the resulting mixture was put into a 1-L kneader equipped with a reflux tube (Irie Shokai's PNV-1 Model), and with stirring at 50° C. in a nitrogen atmosphere at 50 rpm, this was ripened for 5 hours to give a cationized cellulose (ii).
(4) Hydroxypropylation Step The kneader containing 152.6 g of the cationized cellulose (ii) obtained after ripening (unneutralized unpurified product) was heated up to 70° C., and with stirring, 72.5 g of propylene oxide (corresponding to 2.5 mols per mol of AGU, Kanto Chemical's special grade reagent) was dropwise added thereto and reacted for 20 hours until the propylene oxide was consumed and the reflux flow stopped.

After the reaction, the reaction mixture was taken out of the kneader to give 210.6 g of a pale brown crude C-HPC powder. 10.0 g of the crude C-HPC powder was sampled and neutralized with acetic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C-HPC (1).

Through elementary analysis thereof, the chlorine content of the obtained pure C-HPC (1) was 3.4%. The hydroxypropoxy group content according to the above-mentioned "Method for Analysis of Hydroxypropyl Cellulose" was 43.3%. The degree of substitution with cationized ethyleneoxy group and the degree of substitution with propyleneoxy group were 0.30 and 1.8, respectively. The mean degree of polymerization of the pure C-HPC (1) was 739. The results are shown in Table 1.

Production Example 2

Production of C-HPC (2)

This is the same as in Production Example 1 except that the condition of the cationization step (1) was changed as in Table 1, that the cationization step (2) was omitted, and that the condition of the hydroxypropylation step was changed as in Table 1. The results of the obtained pure C-HPC (2) are shown in Table 1.

Production Example 3

Production of C-HPC (3)

This is the same as in Production Example 1 except that the conditions of the cationization step (1), the cationization step (2) and the hydroxypropylation step were changed as in Table 1. The results of the obtained pure C-HPC (3) are shown in Table 1.

Production Example 4

Production of C-HPC (4)

This is the same as in Production Example 1 except that the conditions of the cationization step (1), the cationization step (2) and the hydroxypropylation step were changed as in Table 1. The results of the obtained pure C-HPC (4) are shown in Table 1.

TABLE 1

| | Starting Pulp | | | | Cationization Step (1) | | | | | |
|---|---|---|---|---|---|---|---|---|---|---|
| | Degree of Crystal-linity (%) | Mean Degree of Polymer-ization | Water Content (%) | Amount of Pulp Used (g) | Vibrational Mill | Amount of GMAC Added (g) | Grinding Time (min) | Amount of 24.7% NaOH Added (g) | Amount of 48% NaOH Added (g) | Grinding Time (min) |
| Production Example 1 | 74 | 1770 | 7.0 | 100 | MB-1 | 23.4 | 30 | 20 | — | 60 |
| Production Example 2 | 74 | 1770 | 7.0 | 100 | MB-1 | 60.8 | 12 | — | 14.8 | 120 |
| Production Example 3 | 74 | 1770 | 7.0 | 100 | MB-1 | 23.4 | 12 | — | 6.2 | 60 |
| Production Example 4 | 74 | 1770 | 7.0 | 86 | MB-1 | 20 | 12 | — | 8.8 | 60 |

| | Cationization Step (2) | | | | Hydroxypropylation Step | | | Physical Properties of C-HPC | | |
|---|---|---|---|---|---|---|---|---|---|---|
| | Amount of Cationized Cellulose (i) Added (g) | Amount of GMAC Added (g) | Ripening Temperature (°C.) | Ripening Time (hr) | Amount of Cationized Cellulose (ii) Added (g) | Amount of Propylene Oxide Added (g) | Reaction Time (hr) | Mean Degree of Polymer-ization | Chlorine Content (%) | Content of Hydroxy-propoxy Group (%) |
| Production Example 1 | 128 | 31.3 | 50 | 5 | 152.6 | 72.5 | 20 | 739 | 3.4 | 43.3 |
| Production Example 2 | — | — | — | — | 100*1 | 40.8 | 8 | 539 | 3.0 | 32.5 |
| Production Example 3 | 175 | — | 50 | 5 | 100 | 150 | 18 | 1230 | 1.1 | 62.7 |
| Production Example 4 | 110 | 132 | 50 | 5 | 140 | 20 | 9 | 1326 | 9.3 | 5.2 |

*1 Cationized cellulose (ii) was used in place of cationized cellulose (i).

Production Example 5

Production of C-HPC (5)

(1) Chipping Step

As cellulose, a sheet-like wood pulp (Tembec's Biofloc HV10, having a mean degree of polymerization of 1508, a degree of crystallinity of 74% and a water content of 7.0%) was pelletized with a sheet pelletizer (Horai's "SGG-220") into chips of from 3 to 5 mm square.

(2) Cationization Step (1)

559 g of GMAC (corresponding to 0.52 mols per mol of AGU) and 24 g of ion-exchanged water were added to 989 g (water content 7.0%) of the chip-like pulp obtained in the above (1), and mixed in a plastic bag, and then put into a batch-type vibrational mill (Chuo Kakohki's "FV-10": chamber total volume 35 L; 63 rods of SUS304 each having a diameter of 30 mm and a length of 510 mm and having a circular cross section; filling rate 64%). This was ground for 12 minutes (frequency 20 Hz, vibrational amplitude 8 mm, temperature 10 to 40° C.) thereby giving a powdery mixture of cellulose and GMAC.

136.2 g (corresponding to 0.60 mols per mol of AGU) of granular sodium hydroxide (effective content 100%) was put into the vibrational mill. Again this was ground for 112 minutes to give a cationized cellulose.

(3) Hydroxypropylation Step 95.0 g of the cationized cellulose obtained in the above (2) was put into the kneader equipped with a reflux tube used in Production Example 1, the kneader was heated up to 70° C., and with stirring, 35.4 g (corresponding to 2.0 mols per mol of AGU) of propylene oxide was dropwise added thereto, and the reaction was continued for 7 hours until the propylene oxide was consumed and the reflux flow stopped. After the reaction, the reaction mixture was taken out of the kneader to give 120.6 g of a pale brown crude C-HPC powder.

(4) Cationization Step (2)

16.2 g (corresponding to 3.5 mols per mol of AGU) of GMAC was added to 10.6 g of the crude C-HPC powder obtained in the above (3), mixed in a mortar, and then ripened in a thermostat chamber at 50° C. for 24 hours. The obtained crude C-HPC was dispersed in 100 g of a mixed solvent of water/ethanol/isopropyl alcohol=5/45/50 (by weight), then neutralized with acetic acid added thereto, and purified through precipitation. The precipitate was collected through filtration, and dried under reduced pressure overnight in a drier at 60° C. thereby giving a pale brown bulky crude C-HPC (5).

For the purpose of determining the degree of substitution with propyleneoxy group and with cationized ethyleneoxy group, the product was purified through a dialytic membrane (molecular weight cut off, 1000), and then the aqueous solution was freeze-dried to give a pure C-HPC (5).

Through elementary analysis thereof, the chlorine content of the obtained pure C-HPC (5) was 9.1%. The hydroxypropoxy group content was 25.1%. The degree of substitution with cationized ethyleneoxy group and the degree of substitution with propyleneoxy group were calculated to be 1.00 and 1.3, respectively. The mean degree of polymerization of the pure C-HPC (5) was 464. The results are shown in Table 2.

Production Example 6

Production of C-HPC (6)

This is the same as in Production Example 5 except that the starting pulp was changed as in Table 2, and that the conditions of the cationization step (1), the hydroxypropylation step and the cationization step (2) were changed as in Table 2. The results of the obtained pure C-HPC (6) are shown in Table 2.

added thereto. Further, 101 g (corresponding to 3.0 mols per mol of AGU) of propylene oxide was dropwise added thereto and reacted for 24 hours until the propylene oxide was consumed and the reflux flow stopped. After the reaction, the

TABLE 2

| | Starting Pulp | | | | Cationization Step (1) | | | | | |
|---|---|---|---|---|---|---|---|---|---|---|
| | Degree of Crystallinity (%) | Mean Degree of Polymerization | Water Content (%) | Amount of Pulp Used (g) | Vibrational Mill | Amount of GMAC Added (g) | Grinding Time (min) | Amount of 48% NaOH Added (g) | Amount of Granular NaOH Added (g) | Vibrational Mill |
| Production Example 5 | 74 | 1508 | 7.0 | 989 | FV-10 | 559 | 12 | — | 136.2 | 112 |
| Production Example 6 | 77 | 191 | 7.0 | 100 | MB-1 | 60.8 | 12 | 29.8 | — | 140 |

| | Hydroxypropylation Step | | | Cationization Step (2) | | | | Physical Properties of C-HPC | | |
|---|---|---|---|---|---|---|---|---|---|---|
| | Amount of Cationized Cellulose Used (g) | Amount of Propylene Oxide Added (g) | Reaction Time (hr) | Amount of Crude C-HPC Powder Used (g) | Amount of GMAC Added (g) | Ripening Temperature (° C.) | Ripening Time (hr) | Mean Degree of Polymerization | Chlorine Content (%) | Content of Hydroxypropoxy Group (%) |
| Production Example 5 | 95 | 35.4 | 7 | 10.6 | 16.2 | 50 | 24 | 464 | 9.1 | 25.1 |
| Production Example 6 | 190 | 18 | 2 | 45 | 152 | 50 | 24 | 214 | 15.7 | 3.3 |

Production Example 7

Production of C-HPC (7)

(1) Low-Crystalline Powdery Cellulose Production Step

A sheet-like wood pulp (Tembec's Biofloc HV+, having a mean degree of polymerization of 1770, a degree of crystallinity of 74% and a water content of 7.0%) was shredded with a shredder (Meiko Shokai's "MSX2000-IVP440F") into chips of from 3 to 5 mm square. Subsequently, this was dried under reduced pressure at 50° C. for 12 hours to give a chip-like dry pulp (water content 0.4%).

Next, 100 g of the obtained chip-like dry pulp was put into the batch-type vibrational mill used in Production Example 1. This was ground for 35 minutes at a frequency 20 Hz, a vibrational amplitude of 8 mm, and a temperature falling within a range of from 30 to 70° C. to give a powdery cellulose (having a degree of crystallinity of 0%, a mean degree of polymerization of 836, a mean particle size of 52 μm and a water content of 1.0%).

(2) Cationization Step 46.9 g (corresponding to 0.4 mols per mol of AGU) of GMAC was added to 100 g of the powdery cellulose obtained in the above (1), and mixed in a mortar. Subsequently, 5.14 g (corresponding to 0.1 mols per mol of AGU) of an aqueous 48% sodium hydroxide solution and 18 g of ion-exchanged water were added thereto and mixed. The resulting mixture was put into the kneader used in Production Example 1, and stirred at 50° C. for 4 hours to give 170 g of a cationized cellulose.

(3) Hydroxypropylation Step 170 g of the cationized cellulose obtained in the above (2) was heated at 70° C., and with stirring, 4.7 g (corresponding to 0.1 mols per mol of AGU) of an aqueous 48% sodium hydroxide solution and 16.4 g of ion-exchanged water were cellulose kept a flowable powdery state. 10.0 g of the reaction product was sampled and neutralized with acetic acid to give a pale brown solid. The neutralized product was purified through a dialytic membrane (molecular weight cut off, 1000), and then the aqueous solution was freeze-dried to give a pure C-HPC (7).

Through elementary analysis thereof, the chlorine content of the obtained pure C-HPC (7) was 2.1%. The hydroxypropoxy group content was 49.2%. The degree of substitution with cationized ethyleneoxy group and the degree of substitution with propyleneoxy group were calculated to be 0.18 and 2.0, respectively. The mean degree of polymerization of the pure C-HPC (7) was 832. The results are shown in Table 3.

Production Example 8

Production of C-HPC (8)

This is the same as in Production Example 7 except that the starting pulp was changed as in Table 3, and that the conditions of the low-crystalline powdery cellulose production step, the cationization step and the hydroxypropylation step were changed as in Table 3. The results of the obtained pure C-HPC (8) are shown in Table 3.

Production Example 9

Production of C-HPC (9)

This is the same as in Production Example 7 except that the condition of the hydroxypropylation step was changed as in Table 3. The results of the obtained pure C-HPC (9) are shown in Table 3.

TABLE 3

| | Staring Pulp | | | Low-Crystalline Powdery Cellulose Production Step | | | Physical Properties of Powdery Cellulose | | | |
|---|---|---|---|---|---|---|---|---|---|---|
| | Degree of Crystal- linity (%) | Mean Degree of Polymer- ization | Water Content (%) | Shredding Step Drying Step | Chip-like Dry Pulp Water Content (%) | Grinding Step Grinding Time (min) | Degree of Crystal- linity (%) | Mean Degree of Polymer- ization | Mean Particle Size (μm) | Water Content (%) |
| Production Example 7 | 74 | 1770 | 7.0 | at 50° C. under reduced pressure, for 12 hours | 0.4 | 35 | 0 | 836 | 52 | 1.0 |
| Production Example 8 | 74 | 1420 | 7.0 | at 50° C. under reduced pressure, for 12 hours | 0.4 | 20 | 0 | 574 | 52 | 1.0 |
| Production Example 9 | 74 | 1770 | 7.0 | at 50° C. under reduced pressure, for 12 hours | 0.4 | 35 | 0 | 836 | 52 | 1.0 |

| | Cationization Step | | | Hydroxypropylation Step | | Physical Properties of C-HPC | | |
|---|---|---|---|---|---|---|---|---|
| | Amount of Powdery Cellulose Used (g) | Amount of 48% NaOH Added (g) | Amount of GMAC Added (g) | Amount of 48% NaOH Added (g) | Amount of Propylene Oxide Added (g) | Mean Degree of Polymer- ization | Chlorine Content (%) | Content of Hydroxy- propoxy Group (%) |
| Production Example 7 | 100 | 5.1 | 46.9 | 4.7 | 101 | 832 | 2.1 | 49.2 |
| Production Example 8 | 100 | 10.2 | 33.6 | — | 53.2 | 646 | 2.3 | 37.1 |
| Production Example 9 | 100 | 5.1 | 46.9 | 4.7 | 89 | 779 | 2.2 | 45.7 |

Production Example 10

Production of Cationized Cellulose (1)

A cationized cellulose (1) was produced in the same manner as in Production Example 4 except that the propylene oxide addition was omitted.

Production Example 11

Production of C-HPC (10)

(1) Chipping Step

A sheet-like wood pulp (Tembec's Biofloc HV+, having a mean degree of polymerization of 1481, a degree of crystallinity of 74% and a water content of 4.6%) was pelletized with a sheet pelletizer (Horai's "SGG-220") into chips of from 3 to 5 mm square.

(2) Alkali Cellulose Production Step 100 g of the chip-like pulp obtained in the above step (1) and 23.6 g of 0.7-mm granular NaOH (corresponding to 1.0 mol per mol of AGU) were put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%), and ground therein for 15 minutes (frequency 20 Hz, vibrational amplitude 8 mm, temperature 30 to 70° C.). Thus obtained, the ground cellulose/NaOH mixture (mean particle size of cellulose: 65 μm) was transferred into a mortar, and sprayed with 50 g of water. The water content of the ground cellulose/NaOH mixture was 57% relative to the cellulose therein. This was ground with a pestle at 20° C. for 5 minutes to give an alkali cellulose (mean degree of polymerization: 1175).

(3) Hydroxypropylation Step

The alkali cellulose obtained in the above step (2) was put into a kneader equipped with a reflux tube and a dropping funnel (Irie Shokai's PNV-1 Model, capacity 1.0 L), and 85.7 g of propylene oxide (corresponding to 2.5 mols per mol of AGU) was put thereinto and reacted at 50° C. for 6 hours with stirring. For the reaction, propylene oxide was dropwise added taking 5 hours, and the system was then ripened for 1 hour.

(4) Cationization Step 5.8 g of the reaction mixture obtained in the above step (3) was taken into a mortar, and 2.10 g of aqueous 65% 3-chloro-2-hydroxypropyltrimethylammonium chloride solution (by Yokkaichi Gosei) (corresponding to 0.50 mols per mol of AGU) was added thereto and mixed for 5 minutes, and thereafter this was transferred into a 50-ml glass bottle and reacted therein at 50° C. for 7 hours to give a crude C-HPC.

5.0 g of the crude C-HPC powder was sampled and neutralized with lactic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C-HPC (10).

Through elementary analysis thereof, the chlorine content of the obtained pure C-HPC (10) was 3.3% and the hydroxypropoxy group content was 38.8%. The degree of substitution with cationized ethyleneoxy group and the degree of substitution with propyleneoxy group were calculated to be 0.27 and 1.5, respectively. The mean degree of polymerization was 643. The results are shown in Table 4.

TABLE 4

| | Starting Pulp | | | Alkali Cellulose Production Step | | | | | Physical Properties of Alkali Cellulose | |
|---|---|---|---|---|---|---|---|---|---|---|
| | Degree of Crystal- linity (%) | Mean Degree of Polymer- ization | Water Content (%) | Vibrational Mill | Amount of Pulp Used (g) | Grinding Time (min) | Amount of Granular NaOH Used (g) | Amount of Water Added (g) | Particle Size (μm) | Mean Degree of Polymer- ization |
| Production Example 11 | 74 | 1481 | 4.6 | MB-1 | 100 | 15 | 23.6 | 50 | 65 | 1175 |

| | Hydroxypropylation Step | | | Cationization Step | | | | Physical Properties of C-HPC | | |
|---|---|---|---|---|---|---|---|---|---|---|
| | Amount of Propylene Oxide added (g) | Reaction Temperature (° C.) | Reaction Time (hr) | Amount of Reaction Mixture Used (g) | Amount of Aqueous Ammonium Chloride Solution Used (g)*1 | Reaction Temperature (° C.) | Reaction Time (hr) | Mean Degree of Polymer- ization | Chlorine Content (%) | Content of Hydroxy- propoxy Group (%) |
| Production Example 11 | 85.7 | 50 | 6 | 5.8 | 2.10 | 50 | 7 | 643 | 3.3 | 38.8 |

*1Amount of aqueous 3-chloro-2-hydroxypropyltrimethylammonium chloride solution used (g).

Production Example 12

Production of C-HPC (11)

(1) Low-Crystalline Powdery Cellulose Production Step

A chip-like pulp of from 3 to 5 mm square was obtained in the same manner as in Production Example 11(1). One kg of the obtained chip-like pulp was put into a drier (Advantec Toyo's trade name, VO-402) and dried therein at 105° C. for 2 hours to give a dry chip-like pulp (water content 0.8%).

920 g of the obtained dry chip-like pulp was put into a batch-type vibrational mill (Chuo Kakohki's "FV-10": chamber total volume 35 L; 63 rods of SUS304 each having a diameter of 30 mm and a length of 510 mm and having a circular cross section; filling rate 65%). This was ground for 10 minutes (frequency 20 Hz, vibrational amplitude 8 mm, temperature 10 to 40° C.) to give a powdery cellulose (having a degree of crystallinity of 14%, a mean degree of polymerization of 1198, and a water content of 1.0%).

(2) Alkali Cellulose Production Step 369 g of the powdery cellulose obtained in the above step (1) was put into a mixer (Matsubo's "Ledige Mixer", capacity 5 L), and with stirring at 250 rpm for the main blade and at 2500 rpm for the chopper blade, this was sprayed with 212 g of an aqueous 42.5% sodium hydroxide solution (corresponding to 1.0 mol of NaOH per mol of AGU, and 33% of water relative to cellulose) taking 1.5 minutes. After the spraying, the inner temperature was elevated up to 50° C., and the system was ripened for 3 hours to give an alkali cellulose.

(3) Hydroxypropylation Step 607 g of the alkali cellulose obtained in the above step (2) was heated up to 50° C. in the Ledige mixer with stirring at 50 rpm for the main blade and at 400 rpm for the chopper blade, and thereafter 187 g of propylene oxide (corresponding to 1.6 mols per mol of AGU) was dropwise added thereto taking 3.5 hours. After the addition, this was ripened at 50° C. for 2 hours.

(4) Cationization Step 11.4 g of the reaction mixture obtained in the above step (3) was taken into a mortar, and 4.31 g of an aqueous 65% 3-chloro-2-hydroxypropyltrimethylammonium chloride solution (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C-HPC. The crude C-HPC powder was neutralized, purified and freeze-dried in the same manner as in Production Example 11(4) to give a pure C-HPC (11).

Through elementary analysis thereof, the chlorine content of the obtained pure C-HPC (11) was 4.3%. The hydroxypropoxy group content was 24.3%. The degree of substitution with cationized ethyleneoxy group and the degree of substitution with propyleneoxy group were calculated to be 0.25 and 0.8, respectively. The mean degree of polymerization was 659. The results are shown in Table 5.

Production Example 13

Production of C-HPC (12)

(1) Low-Crystalline Powdery Cellulose Production Step

A powdery cellulose (having a degree of crystallinity of 14%, a mean degree of polymerization of 1198 and a water content of 1.0%) was obtained in the same manner as in Production Example 12(1).

(2) Alkali Cellulose Production Step

An alkali cellulose was obtained in the same manner as in Production Example 12(2), except that 530.5 g of the powdery cellulose obtained in the above step (1) and 307 g of an aqueous 42.5% sodium hydroxide solution (corresponding to 1.0 mol of NaOH per mol of AGU and 34% of water relative to cellulose) were used.

(3) Hydroxypropylation Step 825 g of the alkali cellulose obtained in the above step (2) was heated up to 50° C. with stirring in the above-mentioned Ledige mixer at 50 rpm for the main blade and at 400 rpm for the chopper blade, and thereafter 467 g of propylene oxide (corresponding to 2.6 mols per mol of AGU) was dropwise added thereto taking 6 hours. After the addition, this was ripened at 50° C. for 2 hours.

(4) Cationization Step 12.3 g of the reaction mixture obtained in the above step (3) was taken into a mortar, and 4.31 g of aqueous 65% 3-chloro-2-hydroxypropyltrimethylammonium chloride solution (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C-HPC. The crude C-HPC powder was neutralized, purified and freeze-dried in the same manner as in Production Example 11(4) to give a pure C-HPC (12).

Through elementary analysis thereof, the chlorine content of the obtained pure C-HPC (12) was 2.5%. The hydroxypropoxy group content was 38.5%. The degree of substitution with cationized ethyleneoxy group and the degree of substitution with propyleneoxy group were calculated to be 0.19 and 1.4, respectively. The mean degree of polymerization was 1186. The results are shown in Table 5.

TABLE 5

| | Starting Pulp | | | Low-Crystalline Powdery Cellulose Production Step | | | |
|---|---|---|---|---|---|---|---|
| | Degree of Crystallinity (%) | Mean Degree of Polymerization | Water Content (%) | Vibrational Mill | Drying Time (hr) | Drying Temperature (° C.) | Grinding Time (min) |
| Production Example 12 | 74 | 1481 | 4.6 | FV-10 | 2 | 105 | 10 |
| Production Example 13 | 74 | 1481 | 4.6 | FV-10 | 2 | 105 | 10 |

| | Physical Properties of Powdery Cellulose | | | Alkali Cellulose Production Step | | | |
|---|---|---|---|---|---|---|---|
| | Degree of Crystallinity (%) | Mean Degree of Polymerization | Water Content (%) | Amount of Powdery Cellulose Used (g) | Amount of Aqueous 42.5% NaOH Solution Used (g) | Ripening Temperature (° C.) | Ripening Time (min) |
| Production Example 12 | 14 | 1198 | 1 | 369 | 212 | 50 | 3 |
| Production Example 13 | 14 | 1198 | 1 | 530.5 | 307 | 50 | 3 |

| | Hydroxypropylation Step | | | | Cationization Step | |
|---|---|---|---|---|---|---|
| | Amount of Alkali Cellulose Used (g) | Amount of Propylene Oxide Used (g) | Reaction Temperature (° C.) | Reaction Time (hr) | Amount of Reaction Mixture Used (g) | Amount of Aqueous Ammonium Chloride Solution Used (g)*1 |
| Production Example 12 | 607 | 187 | 50 | 5.5 | 11.4 | 4.31 |
| Production Example 13 | 825 | 467 | 50 | 8 | 12.3 | 4.31 |

| | Cationization Step | | Physical Properties of C-HPC | | |
|---|---|---|---|---|---|
| | Reaction Temperature (° C.) | Reaction Time (hr) | Mean Degree of Polymerization | Chlorine Content (%) | Content of Hydroxypropoxy Group (%) |
| Production Example 12 | 50 | 5 | 659 | 4.3 | 24.3 |
| Production Example 13 | 50 | 5 | 1186 | 2.5 | 38.5 |

*1 Amount of aqueous 3-chloro-2-hydroxypropyltrimethylammonium chloride solution used (g).

The mean degree of polymerization, the degree of substitution with cationized ethyleneoxy group and the degree of substitution with propyleneoxy group of C-HPC obtained in Production Examples 1 to 9 and 11 to 13, and the mean degree of polymerization and the degree of substitution with cationized ethyleneoxy group of the cationized cellulose (1) are summarized in Table 6.

TABLE 6

|  |  | Mean Degree of Polymerization | Degree of Substitution with Cationized EO *1 | Degree of Substitution with PO *2 | 2% Viscosity *3 |
| --- | --- | --- | --- | --- | --- |
| Production Example 1 | C-HPC (1) | 739 | 0.30 | 1.8 | — |
| Production Example 2 | C-HPC (2) | 539 | 0.22 | 1.1 | 171 |
| Production Example 3 | C-HPC (3) | 1230 | 0.11 | 2.9 | — |
| Production Example 4 | C-HPC (4) | 1326 | 0.77 | 0.2 | 13600 |
| Production Example 5 | C-HPC (5) | 464 | 1.00 | 1.3 | 32 |
| Production Example 6 | C-HPC (6) | 214 | 2.36 | 0.2 | 9 |
| Production Example 7 | C-HPC (7) | 832 | 0.18 | 2.0 | — |
| Production Example 8 | C-HPC (8) | 646 | 0.17 | 1.3 | — |
| Production Example 9 | C-HPC (9) | 779 | 0.18 | 1.8 | — |
| Production Example 10 | Cationized Cellulose (1) | 1288 | 0.77 | 0.0 | 1049 |
| Production Example 11 | C-HPC (10) | 643 | 0.27 | 1.5 | — |
| Production Example 12 | C-HPC (11) | 659 | 0.25 | 0.8 | — |
| Production Example 13 | C-HPC (12) | 1186 | 0.19 | 1.4 | — |

*1: Degree of substitution with cationized ethyleneoxy group.
*2: Degree of substitution with propyleneoxy group.
*3: Viscosity of 2% C-HPC (mPa·s)

Examples 1 to 9, 21 to 23, and Comparative Examples 1 to 7

Production and Evaluation of Two-Pack Hair Color (1) Preparation of First Pack

The components shown in Table 7, except higher alcohols and aqueous 28% ammonia solution, were mixed and stirred along with an adequate amount of water. This was heated at 60° C. and completely dissolved. Higher alcohols (cetyl alcohol and stearyl alcohol) were previously mixed and heated at 70° C., and put into the above and emulsified. This was cooled to 40° C., and aqueous 28% ammonia solution and the remaining water were added thereto and uniformly mixed to prepare a first pack. The pH was 10.

The details of the components given in Table 7 are shown below.

C-HPC (1) to (12) (produced in Production Examples 1 to 9, and 11 to 13)

Cationized cellulose (1) (produced in Production Example 10)

Cationized hydroxyethyl cellulose (Amerchol's UCARE POLYMER JR-125)

Dimethyldiallylammonium chloride-acrylamide copolymer (Nalco's MARCOAT 295)

Hydroxyethyl cellulose (Daicel Chemical's HEC-SE 850K)

Hydroxypropyl cellulose (Nippon Soda's CELNY M)

Hexadimethrine bromide (by Sigma-Aldrich)

Hair-coloring dye: 0.6 parts of toluene-2,5-diamine hydrochloride

Oxidation dye intermediate: 0.3 parts of para-aminophenol, 0.3 parts of resorcinol and 0.1 parts of 5-amino-orthocresol, totaling 0.7 parts.

Alkali agent: 1.4 parts of monoethanolamine and 6.5 parts of aqueous 28% ammonia solution, totaling 7.9 parts.

Surfactant: 7.0 parts of laureth-12, 4.0 parts of oleth-30, 5.0 parts of laureth-3 and 3.0 parts of lauric acid, totaling 19.0 parts.

Higher alcohol: 5.8 parts of cetyl alcohol and 5.8 parts of stearyl alcohol, totaling 11.6 parts.

Others: 7.0 parts of propylene glycol, 0.3 parts of sodium sulfite, 0.3 parts of sodium ascorbate, and 0.1 parts of EDTA-2-sodium, totaling 7.7 parts.

(2) Preparation of Second Pack

The following surfactant and others were mixed and stirred with an adequate amount of water. This was heated at 60° C. and completely dissolved. Higher alcohol heated at 70° C. was added thereto and emulsified. This was cooled to 40° C., and aqueous 35% hydrogen peroxide solution and the remaining water were added thereto and uniformly mixed to prepare a second pack. The pH was 4.

Surfactant: 0.5 parts of ceteareth-13 and 1.0 part of laureth-1 sodium sulfate, totaling 1.5 parts.

Higher alcohol: 3.0 parts of cetyl alcohol

Others: 0.1 parts of EDTA-2-sodium, 0.1 parts of phosphoric acid, and 0.2 parts of disodiumhydrogenphosphate, totaling 0.4 parts.

(3) Evaluation of Two-Pack Hair Color

One g of hair tresses washed with plain shampoo having the composition mentioned below was dried with hot air from a drier.

0.4 g of the first pack and 0.6 of the second pack prepared in the above (1) and (2) were mixed to be 1 g in total, and applied to the hair tresses. Subsequently, the hair tresses were left as such at 30° C. for 30 minutes, then rinsed with warm water for 30 seconds, washed with the plain shampoo, and thereafter treated with a plain conditioner having the composition mentioned below.

Subsequently, the hair tresses were towel-dried and combed. Further, this was dried with hot air from a drier and again combed to finish, thereby giving a sample of hair tresses for evaluation. Five panelists tested and evaluated the tresses for the finger combability, body and manageability thereof according to the following evaluation criteria and evaluation methods.

The results are shown in Table 5.

[Composition of Plain Shampoo]

| (Component) | (%) |
| --- | --- |
| Na polyoxyethylene (2 mols) lauryl ether sulfate (40.7% of EMAL E-27C (Kao's trade name, effective ingredient 27%) was added) | 11.0 |

-continued

| (Component) | (%) |
|---|---|
| Cocoyl fatty acid N-methylethanolamide (Kao's trade name, AMINONE C-11S) | 3.0 |
| Citric acid | 0.2 |
| Methylparaben | 0.3 |
| Pure water | balance |
| Total | 100.0 |

[Production of Plain Shampoo]

Na polyoxyethylene (2 mol) lauryl ether sulfate and cocoyl fatty acid N-methylethanolamide were mixed with an adequate amount of water and uniformly mixed. Methylparaben was added thereto and uniformly dissolved. Finally, citric acid and the remaining water were added and uniformly dissolved.

[Composition of Plain Conditioner]

| (Components) | (%) |
|---|---|
| Stearoxypropyltrimethylammonium chloride | 1.0 |
| Cetyl alcohol | 0.6 |
| Stearyl alcohol | 2.3 |
| Propylene glycol | 1.0 |
| Phenoxyethanol | 0.3 |
| Pure water | balance |
| Total | 100.0 |

[Production of Plain Conditioner]

Phenoxyethanol and an adequate amount of water were mixed and heated up to 80° C. Stearoxypropyltrimethylammonium chloride, cetyl alcohol, stearyl alcohol and propylene glycol were previously mixed and heated up to 70° C., and the resulting mixture was added to the above, then emulsified and cooled to room temperature.

Finger Combability
  5: Excellent finger combability.
  4: Good finger combability.
  3: Average.
  2: Bad finger combability.
  1: Extremely bad finger combability.
Body
  5: The hair had excellent body.
  4: The hair had good body.
  3: Average.
  2: The hair had bad body.
  1: The hair had no body at all.
Manageability
  5: The hair was e manageable.
  4: The hair was well manageable.
  3: Average.
  2: The hair was poorly manageable.
  1. The hair was not manageable at all.

(Evaluation Standard: Comparative Example 3 was Given a Standard Score 3.)

The scores given by five panelists were averaged to be the mean score of each sample.

TABLE 7

| | | | Example | | | | | | | | | | | | | Comparative Example | | | | | | |
|---|---|---|---|---|---|---|---|---|---|---|---|---|---|---|---|---|---|---|---|---|---|---|
| | | | 1 | 2 | 3 | 4 | 5 | 6 | 7 | 8 | 9 | 21 | 22 | 23 | 1 | 2 | 3 | 4 | 5 | 6 | 7 |
| Constitutive components (part by mass) | | Two-Pack Hair Color: First Pack | | | | | | | | | | | | | | | | | | | |
| | Component (A) | C-HPC(1) | 1.0 | | | | | | | | | | | | | | | | | | |
| | | C-HPC(2) | | 1.0 | | | | | | | | | | | | | | | | | |
| | | C-HPC(3) | | | 1.0 | | | | | | | | | | | | | | | | |
| | | C-HPC(4) | | | | 1.0 | | | | | | | | | | | | | | | |
| | | C-HPC(5) | | | | | 1.0 | | | | | | | | | | | | | | |
| | | C-HPC(6) | | | | | | 1.0 | | | | | | | | | | | | | |
| | | C-HPC(7) | | | | | | | 1.0 | | | | | | | | | | | | |
| | | C-HPC(8) | | | | | | | | 1.0 | | | | | | | | | | | |
| | | C-HPC(9) | | | | | | | | | 1.0 | | | | | | | | | | |
| | | C-HPC(10) | | | | | | | | | | 1.0 | | | | | | | | | |
| | | C-HPC(11) | | | | | | | | | | | 1.0 | | | | | | | | |
| | | C-HPC(12) | | | | | | | | | | | | 1.0 | | | | | | | |
| | | Cationized Cellulose (1) | | | | | | | | | | | | | 1.0 | | | | | | |
| | | Cationized Hydroxyethyl Cellulose | | | | | | | | | | | | | | 1.0 | | | | | |
| | | Dimethyldiallylammonium Chloride-Acrylamide Copolymer | | | | | | | | | | | | | | | 1.0 | | | | |
| | | Hydroxyethyl Cellulose | | | | | | | | | | | | | | | | 1.0 | | | |
| | | Hydroxypropyl Cellulose | | | | | | | | | | | | | | | | | 1.0 | | |
| | | Hexadimethrine Bromide | | | | | | | | | | | | | | | | | | 1.0 | |
| | Component (B) | Dye: toluene-2,5-diamine hydrochloride | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 |
| | | Oxidation Dye Intermediate | 0.7 | 0.7 | 0.7 | 0.7 | 0.7 | 0.7 | 0.7 | 0.7 | 0.7 | 0.7 | 0.7 | 0.7 | 0.7 | 0.7 | 0.7 | 0.7 | 0.7 | 0.7 | 0.7 |
| | | Alkali Agent | 7.9 | 7.9 | 7.9 | 7.9 | 7.9 | 7.9 | 7.9 | 7.9 | 7.9 | 7.9 | 7.9 | 7.9 | 7.9 | 7.9 | 7.9 | 7.9 | 7.9 | 7.9 | 7.9 |
| | | Surfactant | 19.0 | 19.0 | 19.0 | 19.0 | 19.0 | 19.0 | 19.0 | 19.0 | 19.0 | 19.0 | 19.0 | 19.0 | 19.0 | 19.0 | 19.0 | 19.0 | 19.0 | 19.0 | 19.0 |
| | | Higher Alcohol | 11.6 | 11.6 | 11.6 | 11.6 | 11.6 | 11.6 | 11.6 | 11.6 | 11.6 | 11.6 | 11.6 | 11.6 | 11.6 | 11.6 | 11.6 | 11.6 | 11.6 | 11.6 | 11.6 |
| | | Others | 7.7 | 7.7 | 7.7 | 7.7 | 7.7 | 7.7 | 7.7 | 7.7 | 7.7 | 7.7 | 7.7 | 7.7 | 7.7 | 7.7 | 7.7 | 7.7 | 7.7 | 7.7 | 7.7 |
| | | Pure Water *1 | balance | | | | | | | | | | | | | | | | | | |
| Evaluation Results (after dried) | | Finger combability | 4 | 4 | 4 | 4 | 5 | 3 | 3 | 3 | 3 | 4.6 | 4 | 4.8 | 2.4 | 2 | 2 | 3 | 2 | 2.4 | 3 |
| | | Body | 5 | 5 | 5 | 5 | 5 | 5 | 4 | 4 | 4 | 5 | 5 | 5 | 3.4 | 2 | 2 | 2 | 2.4 | 2 | 3 |
| | | Manageability | 5 | 5 | 5 | 5 | 5 | 5 | 5 | 4.6 | 5 | 5 | 5 | 5 | 3 | 5 | 3.4 | 2 | 3 | 4 | 3 |
| | | Two-Pack Hair Color: Second Pack | | | | | | | | | | | | | | | | | | | |
| Constitutive components (part by mass) | Component (B) | Aqueous 35% Hydrogen Peroxide | 17.0 | | | | | | | | | | | | | | | | | | |
| | | Surfactant | 1.5 | | | | | | | | | | | | | | | | | | |
| | | Higher Alcohol | 3.0 | | | | | | | | | | | | | | | | | | |
| | | Others | 0.4 | | | | | | | | | | | | | | | | | | |
| | | Pure Water *1 | balance | | | | | | | | | | | | | | | | | | |

*1: To be 100 parts by mass in total.

From Table 7, it is known that the hair colors of Examples 1 to 9 and 21 to 23 gave good finger combability, body and manageability to the hair colored with the hair color and dried.

Examples 10 to 14, and Comparative Example 8

Production and Evaluation of Two-Pack Hair Color

Two-pack hair colors each having the composition shown in Table 8 were produced in the same manner as in Example 1. The pH of the first pack was 10, and the pH of the second pack was 4. The results are shown in Table 8.

From Table 8, it is known that the hair colors of Examples 10 to 14 gave good finger combability, body and manageability to the hair colored with the hair color and dried.

Example 15, and Comparative Examples 9 to 11

Production and Evaluation of Two-Pack Hair Color

Two-pack hair colors each having the composition shown in Table 9 were produced in the same manner as in Example 1. The pH of the first pack was 10, and the pH of the second pack was 4. The results are shown in Table 9.

From Table 9, it is known that the two-pack hair color of Example 15 gave good finger combability, body and manageability to the hair colored with the hair color and dried.

TABLE 8

| | | | Example | | | | | Comparative Example |
|---|---|---|---|---|---|---|---|---|
| | | | 10 | 11 | 12 | 13 | 14 | 8 |
| | | Two-Pack Hair Color: First Pack | | | | | | |
| Constitutive components (part by mass) | Component (A) | C-HPC(2) | 0.01 | 0.1 | 0.5 | 5.0 | 10.0 | |
| | Component (B) | Para-aminophenol | 0.3 | 0.3 | 0.3 | 0.3 | 0.3 | 0.3 |
| | | Resorcinol | 0.3 | 0.3 | 0.3 | 0.3 | 0.3 | 0.3 |
| | | 5-Amino-orthocresol | 0.1 | 0.1 | 0.1 | 0.1 | 0.1 | 0.1 |
| | | Toluene-2,5-diamine Hydrochloride | 0.6 | 0.6 | 0.6 | 0.6 | 0.6 | 0.6 |
| | | Ethanolamine | 1.4 | 1.4 | 1.4 | 1.4 | 1.4 | 1.4 |
| | | Aqueous 28% Ammonia | 6.5 | 6.5 | 6.5 | 6.5 | 6.5 | 6.5 |
| | | Laureth-12 | 7.0 | 7.0 | 7.0 | 7.0 | 7.0 | 7.0 |
| | | Oleth-30 | 4.0 | 4.0 | 4.0 | 4.0 | 4.0 | 4.0 |
| | | Laureth-3 | 5.0 | 5.0 | 5.0 | 5.0 | 5.0 | 5.0 |
| | | Lauric Acid | 3.0 | 3.0 | 3.0 | 3.0 | 3.0 | 3.0 |
| | | Cetyl Alcohol | 5.8 | 5.8 | 5.8 | 5.8 | 5.8 | 5.8 |
| | | Stearyl Alcohol | 5.8 | 5.8 | 5.8 | 5.8 | 5.8 | 5.8 |
| | | Propylene Glycol | 7.0 | 7.0 | 7.0 | 7.0 | 7.0 | 7.0 |
| | | Sodium Sulfite | 0.3 | 0.3 | 0.3 | 0.3 | 0.3 | 0.3 |
| | | Sodium Ascorbate | 0.3 | 0.3 | 0.3 | 0.3 | 0.3 | 0.3 |
| | | EDTA-2-Sodium | 0.1 | 0.1 | 0.1 | 0.1 | 0.1 | 0.1 |
| | | Pure Water *1 | balance | balance | balance | balance | balance | balance |
| Evaluation Results (after dried) | | Finger combability | 3.6 | 4 | 4 | 4 | 3.6 | 3 |
| | | Body | 3 | 5 | 5 | 5 | 4 | 3 |
| | | Manageability | 4 | 4 | 5 | 5 | 5 | 3 |
| | | Two-Pack Hair Color: Second pack | | | | | | |
| Constitutive components (part by mass) | Component (B) | Aqueous 35% Hydrogen Peroxide | 17.0 | | | | | |
| | | Ceteareth-13 | 0.5 | | | | | |
| | | Sodium Laureth-1 Sulfate | 1.0 | | | | | |
| | | Cetyl Alcohol | 3.0 | | | | | |
| | | EDTA-2-Sodium | 0.1 | | | | | |
| | | Phosphoric Acid | 0.1 | | | | | |
| | | Disodium Hydrogenphosphate | 0.2 | | | | | |
| | | Pure Water *1 | balance | | | | | |

*1: To make 100 parts by mass in total.

TABLE 9

| | | | Example | Comparative Example | | |
|---|---|---|---|---|---|---|
| | | | 15 | 9 | 10 | 11 |
| | | Two-Pack Hair Color: First Pack | | | | |
| Constitutive components (part by mass) | Component (A) | C-HPC(2) | 0.5 | | | |
| | | Cationized Hydroxyethyl Cellulose | | 0.5 | | |
| | | Dimethyldiallylammonium Chloride-Acrylamide Copolymer | | | 0.5 | |
| | Component (B) | Para-aminophenol | 0.3 | 0.3 | 0.3 | 0.3 |
| | | Resorcinol | 0.3 | 0.3 | 0.3 | 0.3 |
| | | 5-Amino-orthocresol | 0.1 | 0.1 | 0.1 | 0.1 |
| | | Toluene-2,5-diamine Hydrochloride | 0.6 | 0.6 | 0.6 | 0.6 |
| | | Ethanolamine | 0.5 | 0.5 | 0.5 | 0.5 |
| | | Aqueous 28% Ammonia | 6.5 | 6.5 | 6.5 | 6.5 |
| | | Ceteareth-13 | 1.0 | 1.0 | 1.0 | 1.0 |
| | | Stearyltrimethylammonium Chloride | 2.0 | 2.0 | 2.0 | 2.0 |
| | | Cetyl Alcohol | 7.0 | 7.0 | 7.0 | 7.0 |
| | | Propylene Glycol | 4.0 | 4.0 | 4.0 | 4.0 |
| | | Sodium Sulfite | 0.3 | 0.3 | 0.3 | 0.3 |
| | | Sodium Ascorbate | 0.3 | 0.3 | 0.3 | 0.3 |
| | | EDTA-2-Sodium | 0.3 | 0.3 | 0.3 | 0.3 |
| | | Pure Water *1 | balance | balance | balance | balance |
| Evaluation Results (after dried) | | Finger combability | 5 | 2 | 3.4 | 3 |
| | | Body | 5 | 2 | 2.4 | 3 |
| | | Manageability | 4 | 5 | 3.4 | 3 |
| | | Two-Pack Hair Color: Second pack | | | | |
| Constitutive components (part by mass) | Component (B) | Aqueous 35% Hydrogen Peroxide | 17.0 | | | |
| | | Ceteareth-13 | 0.4 | | | |
| | | Stearyltrimethylammonium Chloride | 0.6 | | | |
| | | Cetyl Alcohol | 3.0 | | | |
| | | EDTA-2-Sodium | 0.1 | | | |
| | | Phosphoric Acid | 0.1 | | | |
| | | Disodium Hydrogenphosphate | 0.2 | | | |
| | | Pure Water *1 | balance | | | |

*1: To make 100 parts by mass in total.

Example 16, and Comparative Examples 12 to 14

Production and Evaluation of Two-Pack Hair Color

Two-pack hair colors each having the composition shown in Table 10 were produced in the same manner as in Example 1. The pH of the first pack was 10, and the pH of the second pack was 4. The results are shown in Table 10.

From Table 10, it is known that the two-pack hair colors of Example 16 gave good finger combability, body and manageability to the hair colored with the hair color and dried.

TABLE 10

| | | | Example | Comparative Example | | |
|---|---|---|---|---|---|---|
| | | | 16 | 12 | 13 | 14 |
| | | Two-Pack Hair Color: First Pack | | | | |
| Constitutive components (part by mass) | Component (A) | C-HPC(2) | 0.5 | | | |
| | | Cationized Hydroxyethyl Cellulose | | 0.5 | | |
| | | Dimethyldiallylammonium Chloride-Acrylamide Copolymer | | | 0.5 | |
| | Component (B) | Para-aminophenol | 0.3 | 0.3 | 0.3 | 0.3 |
| | | Resorcinol | 0.3 | 0.3 | 0.3 | 0.3 |
| | | 5-Amino-orthocresol | 0.1 | 0.1 | 0.1 | 0.1 |
| | | Toluene-2,5-diamine Hydrochloride | 0.6 | 0.6 | 0.6 | 0.6 |
| | | Aqueous 28% Ammonia | 6.5 | 6.5 | 6.5 | 6.5 |
| | | Ethanolamine | 0.5 | 0.5 | 0.5 | 0.5 |
| | | Ceteareth-13 | 1.0 | 1.0 | 1.0 | 1.0 |
| | | Sodium Laureth-1 Sulfate | 3.0 | 3.0 | 3.0 | 3.0 |
| | | Cetyl Alcohol | 7.0 | 7.0 | 7.0 | 7.0 |
| | | Propylene Glycol | 4.0 | 4.0 | 4.0 | 4.0 |
| | | Sodium Sulfite | 0.3 | 0.3 | 0.3 | 0.3 |

TABLE 10-continued

|  |  |  | Example | Comparative Example | | |
|---|---|---|---|---|---|---|
|  |  |  | 16 | 12 | 13 | 14 |
|  |  | Sodium Ascorbate | 0.3 | 0.3 | 0.3 | 0.3 |
|  |  | EDTA-2-Sodium | 0.3 | 0.3 | 0.3 | 0.3 |
|  |  | Pure Water *1 | balance | balance | balance | balance |
| Evaluation Results | | Finger combability | 4 | 2 | 2 | 3 |
| (after dried) | | Body | 4 | 3 | 2 | 3 |
|  |  | Manageability | 4 | 4 | 4 | 3 |
|  |  | Two-Pack Hair Color: Second pack | | | | |
| Constitutive components (part by mass) | Component (B) | Aqueous 35% Hydrogen Peroxide | 17.0 | | | |
|  |  | Ceteareth-13 | 0.5 | | | |
|  |  | Sodium Laureth-1 Sulfate | 1.0 | | | |
|  |  | Cetyl Alcohol | 3.0 | | | |
|  |  | EDTA-2-Sodium | 0.1 | | | |
|  |  | Phosphoric Acid | 0.1 | | | |
|  |  | Disodium Hydrogenphosphate | 0.2 | | | |
|  |  | Pure Water *1 | balance | | | |

*1: To make 100 parts by mass in total.

Example 17 and Comparative Example 15

Production and Evaluation of One-Pack Hair Color

C-HPC (2), hydroxypropylxanthane gum (Dai-Nippon Sumitomo Pharma's Rhaball Gum EX) and an adequate amount of water were mixed and stirred. These were dissolved by heating at 60° C. An aqueous 71% glycolic acid solution, Black 401, Orange 205, ethanol, glycerin, laureth-13, and PEG-11 methyl ether dimethicone (Shin-etsu Chemical's KF6011) were added thereto and stirred until dissolution. This was cooled to 40° C., and an adequate amount of water was added thereto and uniformly mixed to give a one-pack hair color having the composition shown in Table 11. The pH was 3.

One g of white hair tresses washed with the same plain shampoo as in Example 1 were dried with hot air from a drier. One g of the one-pack hair color composition was applied to the hair tresses. Subsequently, the hair tresses were left as such at 30° C. for 30 minutes, then rinsed with warm water for 30 seconds, washed with the same plain shampoo as in Example 1, and treated with the same plain conditioner as in Example 1. Subsequently, the hair tresses were towel-dried, combed, further dried with hot air from a drier and again combed to finish, thereby giving a sample of hair tresses for evaluation. The sample was evaluated in the same manner as in Example 1. The results are shown in Table 11.

From Table 11, it is known that the one-pack hair color of Example 17 gave good finger combability, body and manageability to the hair colored therewith and dried.

TABLE 11

|  |  | One-Pack Hair Color | Example 17 | Comparative Example 15 |
|---|---|---|---|---|
| Constitutive components (part by mass) | Component (A) | C-HPC(2) | 0.5 | |
|  | Component (B) | Black 401 | 0.5 | 0.5 |
|  |  | Orange 205 | 0.3 | 0.3 |
|  |  | Laureth-13 | 0.3 | 0.3 |
|  |  | PEG-11 Methyl Ether Dimethicone | 1.6 | 1.6 |
|  |  | 71% Glycolic Acid | 5.7 | 5.7 |
|  |  | Ethanol | 7 | 7 |
|  |  | Glycerin | 1 | 1 |
|  |  | Hydroxypropylxanthane Gum | 1.4 | 1.4 |
|  |  | Pure Water *1 | balance | balance |
| Evaluation Results (after dried) | | Finger combability | 5 | 3 |
|  |  | Body | 5 | 3 |
|  |  | Manageability | 5 | 3 |

*1: To make 100 parts by mass in total.

Example 18 and Comparative Example 16

Production and Evaluation of One-Pack Hair Bleach

C-HPC (2), ceteth-40, PEG (60)-hydrogenated castor oil, Polysorbate-40, dipropylene glycol, EDTA-4-sodium, sodium dihydrogenphospahte, phosphoric acid and an adequate amount of water were mixed and stirred. These were completely dissolved by heating at 60° C. Cetyl alcohol heated at 70° C. was added thereto and emulsified. This was cooled to 40° C., and aqueous 35% hydrogen peroxide and the remaining water were added thereto and uniformly mixed to give a one-pack hair bleach having the composition shown in Table 12. The pH was 3.

One g of black hair tresses washed with the same plain shampoo as in Example 1 were dried with hot air from a drier. One g of the one-pack hair bleach composition obtained in the above was applied to the hair tresses. Subsequently, the hair tresses were left as such at 30° C. for 30 minutes, then rinsed with warm water for 30 seconds, washed with the same plain shampoo as in Example 1, and treated with the same plain conditioner as in Example 1. Subsequently, the hair tresses were towel-dried, combed, further dried with hot air from a drier and again combed to finish, thereby giving a sample of hair tresses for evaluation. The sample was evaluated in the same manner as in Example 1. The results are shown in Table 12.

From Table 12, it is known that the one-pack hair bleach of Example 18 gave good finger combability, body and manageability to the hair bleached therewith and dried.

(2) Preparation of Second Pack

Sodium bromate, propylene glycol, surfactants (ceteareth-13, laureth-3), keratin hydrolyzates (Seiwa Chemical's Promois (effective content 10%) was added in an amount of 1.0%) and an adequate amount of water were mixed and stirred until complete dissolution. Amodimethicone (Toray Dow Corning's SM8904 (effective content 40%) was added in an amount of 1.25%) was added thereto and uniformly mixed to prepare the second pack. The pH was 7.

(3) Evaluation of Permanent Wave Agent

Black straight hair tresses of an adult woman, which had had no experience of chemical treatment and had a length of

TABLE 12

| | | One-Pack Hair Bleach | Example 18 | Comparative Example 16 |
|---|---|---|---|---|
| Constitutive components (part by mass) | Component (A) | C-HPC(2) | 0.5 | |
| | Component (B) | Aqueous 35% Hydrogen Peroxide | 5.9 | 5.9 |
| | | Ceteth-40 | 3 | 3 |
| | | PEG(60)-Hydrogenated Castor Oil | 0.5 | 0.5 |
| | | Polysorbate-40 | 0.5 | 0.5 |
| | | Cetyl Alcohol | 10 | 10 |
| | | Dipropylene Glycol | 2 | 2 |
| | | EDTA-4-Sodium | 0.1 | 0.1 |
| | | Disodium Hydrogenphosphate | 0.1 | 0.1 |
| | | Phosphoric Acid | 0.2 | 0.2 |
| | | Pure Water *1 | balance | balance |
| Evaluation Results (after dried) | | Finger combability | 4 | 3 |
| | | Body | 4 | 3 |
| | | Manageability | 5 | 3 |

*1: To make 100 parts by mass in total.

Example 19 and Comparative Examples 17 to 22

Production and Evaluation of Permanent Wave Agent (1) Preparation of First Pack

As shown in Table 13, the other components than 50% ammonium thioglycolate and 28% ammonia were mixed with an adequate amount of water and stirred until complete dissolution. 50% ammonium thioglycolate, 28% ammonia and the remaining water were added thereto and stirred for complete dissolution, thereby preparing the first pack. The pH was 9.

The details of the components shown in Table 13 are as follows:

C-HPC (2) (produced in Production Examples 2)

Cationized hydroxyethyl cellulose (Amerchol's UCARE POLYMER JR-125)

Dimethyldiallylammonium chloride-acrylamide copolymer (Nalco's MARCOAT 295)

Hydroxyethyl cellulose (Daicel Chemical's HEC-SE 850K)

Hydroxypropyl cellulose (Nippon Soda's CELNY M)

Hexadimethrine bromide (by Sigma-Aldrich)

about 26 cm and a weight of 10 g, were tested here as a sample. This was treated with the same plain shampoo as in Example 1, rinsed with running water and air-dried. Two g of the sample hair tresses were trimmed to have a uniform thickness and a width of 2 cm. One end of the sample was fixed to a plastic board having a width of 2 cm with an adhesive, thereby preparing test hair tresses.

Thus prepared, the hair tresses were treated with the same plain shampoo as in Example 1, towel-dried and combed. The hair tresses were wound around a rod having a diameter of 9 mm (Dariya's Venezel Cold Rod No. 6), 2 g of the first pack was applied thereto and left as such at 30° C. for 15 minute. Further, 2 g of the second pack was applied thereto and left as such as 30° C. for 15 minutes. The treated hair tresses were rinsed with warm water for 30 seconds. Subsequently, these were towel-dried, combed, dried with hot air from a drier, and again combed to finish, thereby preparing hair tresses for evaluation.

This was evaluated in the same manner as in Example 1, and the results are shown in Table 13.

From Table 13, it is known that the permanent wave agent of Example 19 gave good finger combability, body and manageability to the hair treated and dried.

TABLE 13

| | | | Example | Comparative Example | | | | | |
|---|---|---|---|---|---|---|---|---|---|
| | | | 19 | 17 | 18 | 19 | 20 | 21 | 22 |
| | | Permanent Wave Agent, First Pack | | | | | | | |
| Constitutive components (part by mass) | Component (A) | C-HPC(2) | 0.5 | | | | | | |
| | | Cationized Hydroxyethyl Cellulose | | 0.5 | | | | | |
| | | Dimethyldiallylammonium Chloride-Acrylamide Copolymer | | | 0.5 | | | | |
| | | Hydroxyethyl Cellulose | | | | 0.5 | | | |
| | | Hydroxypropyl Cellulose | | | | | 0..5 | | |
| | | Hexadimethrine Bromide | | | | | | 0.5 | |
| | Component (B) | 50% Ammonium Thioglycolate | 12 | 12 | 12 | 12 | 12 | 12 | 12 |
| | | Ammonium Hydrogencarbonate | 2.5 | 2.5 | 2.5 | 2.5 | 2.5 | 2.5 | 2.5 |
| | | Aqueous 28% ammonia | 1.5 | 1.5 | 1.5 | 1.5 | 1.5 | 1.5 | 1.5 |
| | | Monoethanolamine | 1 | 1 | 1 | 1 | 1 | 1 | 1 |
| | | Ceteareth-13 | 1 | 1 | 1 | 1 | 1 | 1 | 1 |
| | | Ethanol | 5 | 5 | 5 | 5 | 5 | 5 | 5 |
| | | Propylene Glycol | 5 | 5 | 5 | 5 | 5 | 5 | 5 |
| | | EDTA-2-Sodium | 0.5 | 0.5 | 0.5 | 0.5 | 0.5 | 0.5 | 0.5 |
| | | Pure Water *1 | balance | balance | balance | balance | balance | balance | balance |
| Evaluation Results (after dried) | | Finger combability | 5 | 3 | 3 | 2 | 4 | 2 | 3 |
| | | Body | 4 | 4 | 2 | 2 | 2 | 2 | 3 |
| | | Manageability | 5 | 2 | 2 | 3 | 4 | 2 | 3 |
| | | Permanent Wave Agent, Second Pack | | | | | | | |
| Constitutive components (part by mass) | Component (B) | Sodium Bromate | 7.5 | | | | | | |
| | | Ceteareth-13 | 0.75 | | | | | | |
| | | Laureth-3 | 0.25 | | | | | | |
| | | Amodimethicone | 0.5 | | | | | | |
| | | Propylene Glycol | 5 | | | | | | |
| | | Keratin Hydrolyzate | 0.1 | | | | | | |
| | | Pure Water *1 | balance | | | | | | |

*1: To make 100 parts by mass in total.

Example 20 and Comparative Examples 23 to 28

Production and Evaluation of Hair Relaxer (1) Preparation of First Pack

As shown in Table 14, the other components than 50% ammonium thioglycolate were mixed with an adequate amount of water and stirred until complete dissolution. 50% ammonium thioglycolate and the remaining water were added thereto and stirred for complete dissolution, thereby preparing the first pack. The pH was 9.

(2) Preparation of Second Pack

Lactic acid, β-naphthalenesulfonic acid, benzyloxyethanol, ethanol, ceteareth-13 and an adequate amount of water were mixed and stirred until complete dissolution. Next, an aqueous 48% sodium hydroxide solution was added thereto, stirred and mixed. Further, aqueous 35% hydrogen peroxide and the remaining water were added and stirred until complete dissolution to prepare a second pack. The pH was 3.

(3) Evaluation of Hair Relaxer

Unruly hair tresses provided by a Japanese adult woman, having a length of 26 cm and a weight of 10 g, were tested here as a sample. This was treated with the same plain shampoo as in Example 1, rinsed with running water and air-dried. Two g of the sample hair tresses were trimmed to have a uniform thickness and a width of 2 cm. One end of the sample was fixed to a plastic board having a width of 2 cm with an adhesive, thereby preparing test hair tresses.

Thus prepared, the hair tresses were treated with the same plain shampoo as in Example 1, towel-dried and combed. 1.5 g of the first pack was applied to the hair tresses, then left as such at 25° C. for 15 minutes, thereafter rinsed with warm-water for 30 seconds, and towel-dried. Subsequently, the hair tresses were treated with a high-temperature hair iron set at 130° C. Next, 1.5 g of the second pack was applied thereto and left as such at 25° C. for 5 minutes. Thus treated, the hair tresses were rinsed with warm water for 30 seconds. Subsequently, these were towel-dried, combed, dried with hot air from a drier, and again combed to finish, thereby preparing hair tresses for evaluation.

This was evaluated in the same manner as in Example 1, and the results are shown in Table 14.

From Table 14, it is known that the hair relaxer of Example 20 gave good finger combability, body and manageability to the hair treated with the hair relaxer and dried.

TABLE 14

|  |  |  | Example | Comparative Example | | | | | |
|---|---|---|---|---|---|---|---|---|---|
|  |  |  | 20 | 23 | 24 | 25 | 26 | 27 | 28 |
|  |  | Hair Relaxer, First Pack |  |  |  |  |  |  |  |
| Constitutive components (part by mass) | Component (A) | C-HPC(2) | 0.5 |  |  |  |  |  |  |
|  |  | Cationized Hydroxyethyl Cellulose *1 |  | 0.5 |  |  |  |  |  |
|  |  | Dimethyldiallylammonium Chloride-Acrylamide Copolymer *2 |  |  | 0.5 |  |  |  |  |
|  |  | Hydroxyethyl Cellulose *3 |  |  |  | 0.5 |  |  |  |
|  |  | Hydroxypropyl Cellulose *4 |  |  |  |  | 0..5 |  |  |
|  |  | Hexadimethrine Bromide *5 |  |  |  |  |  | 0.5 |  |
|  | Component (B) | 50% Ammonium Thioglycolate | 13 | 13 | 13 | 13 | 13 | 13 | 13 |
|  |  | Monoethanolamine | 2 | 2 | 2 | 2 | 2 | 2 | 2 |
|  |  | Ammonium Hydrogencarbonate | 2 | 2 | 2 | 2 | 2 | 2 | 2 |
|  |  | β-naphthalenesulfonic acid | 2 | 2 | 2 | 2 | 2 | 2 | 2 |
|  |  | Benzyloxyethanol | 3.5 | 3.5 | 3.5 | 3.5 | 3.5 | 3.5 | 3.5 |
|  |  | Ethanol | 4 | 4 | 4 | 4 | 4 | 4 | 4 |
|  |  | Propylene Glycol | 5 | 5 | 5 | 5 | 5 | 5 | 5 |
|  |  | EDTA-2-Sodium | 0.5 | 0.5 | 0.5 | 0.5 | 0.5 | 0.5 | 0.5 |
|  |  | Pure Water *6 | balance | balance | balance | balance | balance | balance | balance |
| Evaluation Results (after dried) |  | Finger combability | 4.6 | 3 | 2.4 | 3.4 | 3 | 3.4 | 3 |
|  |  | Body | 4 | 2 | 3 | 3 | 3 | 3 | 3 |
|  |  | Manageability | 5 | 4 | 2 | 2 | 3 | 2 | 3 |
|  |  | Hair Relaxer, Second Pack |  |  |  |  |  |  |  |
| Constitutive components (part by mass) | Component (B) | 35% Hydrogen Peroxide | 1.8 |  |  |  |  |  |  |
|  |  | Aqueous 48% Sodium Hydroxide Solution | 0.1 |  |  |  |  |  |  |
|  |  | Ceteareth-13 | 1 |  |  |  |  |  |  |
|  |  | Lactic Acid | 4.5 |  |  |  |  |  |  |
|  |  | β-naphthalenesulfonic acid | 1.5 |  |  |  |  |  |  |
|  |  | Benzyloxyethanol | 3.5 |  |  |  |  |  |  |
|  |  | Ethanol | 10 |  |  |  |  |  |  |
|  |  | Pure Water *6 | balance |  |  |  |  |  |  |

*1: Amerchol's UCARE POLYMER JR-125
*2: Nalco's MARCOAT 295 (effective content 40%) was added in an amount of 1.25%.
*3: Daicel Chemical's HEC SE-850K
*4: Nippon Soda's CELNY M
*5: Sigma Aldrich's hexadimethrine bromide
*6: To make 100 parts by mass in total.

INDUSTRIAL APPLICABILITY

The hair treatment composition of the present invention is favorably usable in the field of hair color, hair bleach, permanent wave agent, straight perm agent, sustainable hair set agent, hair relaxer, etc.

The invention claimed is:

1. A method of treating hair, the method comprising a step of applying a hair treatment composition to hair in an effective amount to provide body to the hair, wherein the hair treatment composition comprises:

a cationized hydroxypropyl cellulose (A); and at least one treating agent (B) selected from the group consisting of a hair-coloring dye, an oxidizing agent, an alkali agent and a keratin-reducing agent, wherein the cationized hydroxypropyl cellulose (A) has an anhydroglucose-derived main chain represented by the following general formula (1), and has a degree of substitution with cationized ethyleneoxy group of from 0.01 to 2.9 and a degree of substitution with propyleneoxy group of from 0.1 to 4.0:

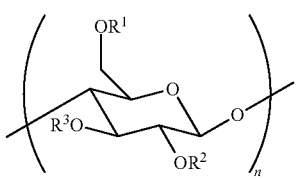
(1)

wherein $R^1$, $R^2$ and $R^3$ each independently represent a substituent having a cationized ethyleneoxy group and a propyleneoxy group represented by the following general formula (2), n indicates a mean degree of polymerization of anhydroglucose and is a number of from 50 to 5000;

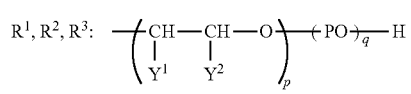
(2)

wherein one of Y¹ and Y² is a hydrogen atom and the other is a cationic group represented by the following general formula (3), PO represents a propyleneoxy group; p indicates the number of cationized ethyleneoxy groups ((—CH(Y¹)—CH(Y²)—O—) in the general formula (2) and q indicates the number of propyleneoxy groups (—PO—) therein, each being 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer;

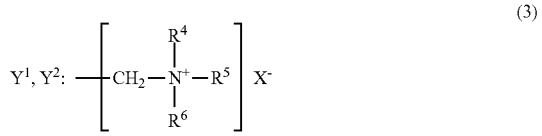

(3)

wherein R⁴, R⁵ and R⁶ each independently represent a linear or branched alkyl group having from 1 to 3 carbon atoms, X⁻ represents an anionic group.

2. The method of treating hair according to claim 1, wherein the content of the cationized hydroxypropyl cellulose (A) is from 0.001 to 20% by mass.

3. The method of treating hair according to claim 1, wherein the mean degree of polymerization of anhydroglucose is a number of from 400 to 1000.

4. The method of treating hair according to claim 1, wherein the cationized hydroxypropyl cellulose (A) is obtained by the following steps (a-1) to (a-3):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A).

5. The method of treating hair according to claim 1, wherein the cationized hydroxypropyl cellulose (A) is obtained by the following steps (b-1) to (b-4):

Step (b-1): a step of processing a cellulose-containing raw material with a grinder to give a cellulose-containing raw material that comprises a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) and propylene oxide to give a hydroxypropyl cellulose, Step (b-4): a step of reacting the hydroxypropyl cellulose obtained in the step (b-3) with a cationizing agent to give the cationized hydroxypropyl cellulose (A).

6. The method of treating hair according to claim 1, wherein the cationized hydroxypropyl cellulose (A) is obtained by the following steps (c-1) to (c-4):

Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

7. The method according to claim 1, wherein the method is a hair coloring method.

8. The method according to claim 1, wherein the method is a hair perm method.

9. The method of treating hair according to claim 1, wherein the degree of substitution with cationized ethyleneoxy group is from 0.19 to 2.9.

10. The method of treating hair according to claim 1, wherein the degree of substitution with cationized ethyleneoxy group is from 0.19 to 1.00.

11. The method of treating hair according to claim 1, wherein the degree of substitution with propyleneoxy group is from 1.3 to 1.5.

12. The method of treating hair according to claim 1, wherein the degree of substitution with cationized ethyleneoxy group is from 0.19 to 1.00, and the degree of substitution with propyleneoxy group is from 1.3 to 1.5.

13. A method of providing body to hair, the method comprising a step of applying a hair treatment composition to hair in an effective amount to provide body to the hair, wherein the hair treatment composition comprises:

a cationized hydroxypropyl cellulose (A); and at least one treating agent (B) selected from the group consisting of a hair-coloring dye, an oxidizing agent, an alkali agent and a keratin-reducing agent, wherein the cationized hydroxypropyl cellulose (A) has an anhydroglucose-derived main chain represented by the following general formula (1), and has a degree of substitution with cationized ethyleneoxy group of from 0.01 to 2.9 and a degree of substitution with propyleneoxy group of from 0.1 to 4.0:

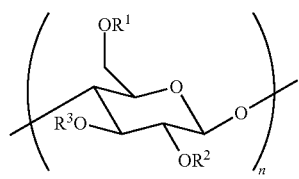

(1)

wherein $R^1$, $R^2$ and $R^3$ each independently represent a substituent having a cationized ethyleneoxy group and a propyleneoxy group represented by the following general formula (2), n indicates a mean degree of polymerization of anhydroglucose and is a number of from 50 to 5000;

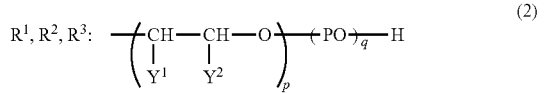

(2)

wherein one of $Y^1$ and $Y^2$ is a hydrogen atom and the other is a cationic group represented by the following general formula (3), PO represents a propyleneoxy group; p indicates the number of cationized ethyleneoxy groups ((—CH($Y^1$)—CH($Y^2$)—O—) in the general formula (2) and q indicates the number of propyleneoxy groups (—PO—) therein, each being 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer;

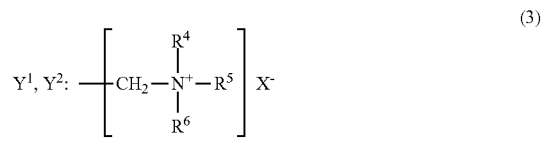

(3)

wherein $R^4$, $R^5$ and $R^6$ each independently represent a linear or branched alkyl group having from 1 to 3 carbon atoms, $X^-$ represents an anionic group).

* * * * *